US010213463B2

(12) United States Patent
Jones et al.

(10) Patent No.: US 10,213,463 B2
(45) Date of Patent: Feb. 26, 2019

(54) COMPOSITIONS FOR BIOLOGICAL SYSTEMS AND METHODS FOR PREPARING AND USING THE SAME

(71) Applicant: SMART SURGICAL, Inc., Boise, ID (US)

(72) Inventors: Christopher D. Jones, Eagle, ID (US); Nathan Quintanar, Boise, ID (US)

(73) Assignee: SMART Surgical, Inc., Boise, ID (US)

( * ) Notice: Subject to any disclaimer, the term of this patent is extended or adjusted under 35 U.S.C. 154(b) by 0 days.

(21) Appl. No.: 15/675,542

(22) Filed: Aug. 11, 2017

(65) Prior Publication Data
US 2017/0354684 A1   Dec. 14, 2017

Related U.S. Application Data

(63) Continuation of application No. 15/619,467, filed on Jun. 10, 2017.

(60) Provisional application No. 62/349,633, filed on Jun. 13, 2016.

(51) Int. Cl.
A61K 35/28     (2015.01)
A61K 35/17     (2015.01)
A61K 47/02     (2006.01)
A61K 47/20     (2006.01)
A61K 47/26     (2006.01)
A61K 47/42     (2017.01)
A61K 38/18     (2006.01)
C12N 5/00      (2006.01)
A61K 35/12     (2015.01)

(52) U.S. Cl.
CPC .............. A61K 35/17 (2013.01); A61K 35/28 (2013.01); A61K 38/18 (2013.01); A61K 47/02 (2013.01); A61K 47/20 (2013.01); A61K 47/26 (2013.01); A61K 47/42 (2013.01); C12N 5/0037 (2013.01); A61K 2035/124 (2013.01); C12N 2500/34 (2013.01); C12N 2500/90 (2013.01)

(58) Field of Classification Search
CPC .. A61K 2035/124; A61K 35/17; A61K 35/28; A61K 47/02; A61K 47/20; A61K 47/26; A61K 47/42; A61K 38/1808; A61K 38/1825; A61K 38/185; A61K 38/1866; A61K 38/191; A61K 38/195; A61K 38/204; A61K 38/2046; A61K 38/206; A61K 38/2086; A61K 38/212; A61K 38/217; A61K 9/0024
See application file for complete search history.

(56) References Cited

U.S. PATENT DOCUMENTS

| | | | |
|---|---|---|---|
| 5,543,316 A | 8/1996 | Zawadzka et al. | |
| 5,599,719 A | 2/1997 | Woiszwillo et al. | |
| 5,723,281 A | 3/1998 | Segall et al. | |
| 5,733,894 A | 3/1998 | Segall et al. | |
| 6,153,582 A | 11/2000 | Skelnik | |
| 6,555,543 B2* | 4/2003 | Bar-Or | A61K 31/495 514/255.02 |
| 7,160,723 B2 | 1/2007 | Collins et al. | |
| 7,247,314 B2 | 7/2007 | Hnojewyj et al. | |
| 8,778,679 B2 | 7/2014 | Silva et al. | |
| 9,241,959 B2 | 1/2016 | Tang | |
| 9,283,084 B1* | 3/2016 | O'Hara | A61F 2/447 |
| 9,387,283 B2 | 7/2016 | Hariri | |
| 9,592,258 B2 | 3/2017 | Seyda et al. | |
| 2005/0255592 A1 | 11/2005 | Collins et al. | |
| 2005/0265980 A1 | 12/2005 | Chen et al. | |
| 2006/0281174 A1 | 12/2006 | Xu et al. | |
| 2007/0249047 A1 | 10/2007 | McKenna et al. | |
| 2009/0229463 A1 | 1/2009 | Collins | |
| 2009/0291494 A1 | 11/2009 | Collins | |
| 2010/0008992 A1* | 1/2010 | Ichim | A61K 38/18 424/488 |
| 2010/0172950 A1* | 7/2010 | Sabetsky | A61K 9/0024 514/1.1 |
| 2010/0278725 A1 | 11/2010 | Liu et al. | |
| 2010/0303774 A1* | 12/2010 | Hedrick | A61L 27/3834 424/93.7 |
| 2011/0274663 A1 | 11/2011 | Shirono et al. | |
| 2012/0100108 A1* | 4/2012 | Bartel | A61K 35/28 424/93.3 |
| 2012/0276632 A1 | 11/2012 | Strunk et al. | |
| 2013/0323712 A1 | 12/2013 | Sato et al. | |

(Continued)

FOREIGN PATENT DOCUMENTS

WO   WO2014075593 A9   5/2014
WO   WO2016/205227 A1  12/2016

OTHER PUBLICATIONS

Agu, C., Soares, F., Alderton, A., Patel, M., Ansari, R., Patel, S., Forrest, S., Yang, F., Lineham, J., Vallier, L., Kirton, C., "Successful Generation of Human Induced Pluripotent Stem Cell Lines from Blood Samples Held at Room Temperature for up to 40 hr", Stem Cell Reports, Oct. 13, 2015, pp. 660-671, vol. 5, Cell Press, Cambridge, U.S.

Lee, H., Morin, P., Xia, W., "Peripheral blood mononuclear cell-converted induced pluripotent stem cells (iPSCs) from an early onset Alzheimer's patient", Stem Cell Research, 2016, pp. 213-215, vol. 16, Elsevier, Oxford, UK.

McDonald, E., "Stability of Dextrose Solutions of Varying pH", Journal of Research of the National Bureau of Standards, Sep. 1950, pp. 200-203, vol. 45, No. 3, National Bureau of Standards and Technology (NIST), Gaithersburg, USA.

(Continued)

Primary Examiner — Lisa J Hobbs
(74) Attorney, Agent, or Firm — Blair Walker IP Services, LLC

(57) ABSTRACT

A method for performing a therapy in a subject includes providing a composition including a solution having a first volume and including a low pH fluid base including dextrose, and albumin, wherein the concentration of albumin in the solution is between about 10 mg/ml and about 150 mg/ml, and implanting within, near, or adjacent tissue of the subject an effective amount of the composition.

25 Claims, 11 Drawing Sheets

(56) References Cited

U.S. PATENT DOCUMENTS

| | | |
|---|---|---|
| 2014/0044792 A1 | 2/2014 | Lacza et al. |
| 2014/0286913 A1* | 9/2014 | Bar-Or .............. A61K 31/495 424/93.7 |
| 2015/0044176 A1 | 2/2015 | Rezner |
| 2015/0110749 A1 | 4/2015 | Vacanti et al. |
| 2015/0152385 A1 | 6/2015 | Sanchez-Schmitz et al. |
| 2015/0208643 A1 | 7/2015 | Keshavjee et al. |
| 2015/0329832 A1 | 11/2015 | Senda et al. |
| 2015/0366932 A1* | 12/2015 | Bar-Or .................. C07K 14/76 514/15.2 |
| 2016/0068815 A1 | 3/2016 | Larsson et al. |
| 2016/0235790 A1 | 8/2016 | Gurney et al. |
| 2016/0304837 A1 | 10/2016 | Huang et al. |
| 2017/0065745 A1 | 3/2017 | Brown et al. |

OTHER PUBLICATIONS

Machine Translation of WO2014075593, Jia, Google Patents, Aug. 8, 2017 (7 pages).

PCT International Search Report and Written Opinion for PCT/US2017/037055, SMART Surgical, Inc., PCT/ISA/220, 210, and 237 dated Oct. 18, 2017 (49 pages).

Basford, C., Forraz, N., Habibollah, S., Hanger, K., McGuckin, C., "Umbilical cord blood processing using Prepacyte-CB increases haematopoietic progenitor cell availability over conventional Hetastarch separation", Cell Proliferation , Dec. 2009, pp. 751-761, vol. 42, No. 6, Blackwell Publishing Ltd., Oxford, UK.

"Burst Biologics Initiates Clinical Study in Foot and Ankle Surgery Patients", Apr. 25, 2017, Burst Biologics/SMART Surgical.

* cited by examiner

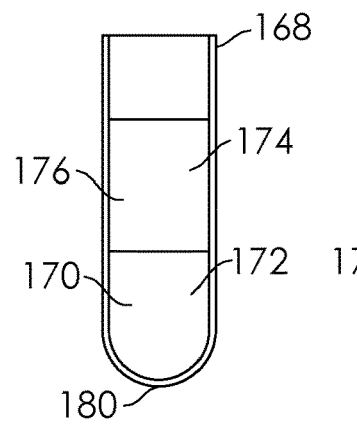 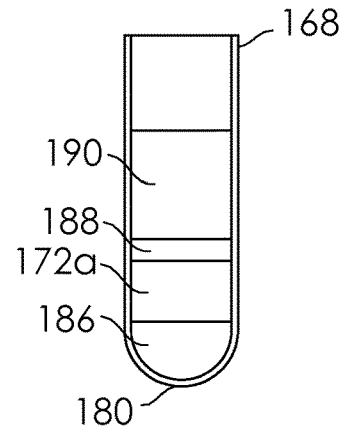 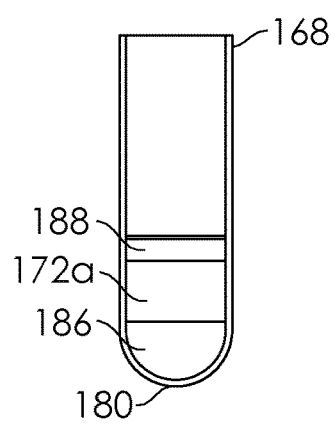
FIG. 7   FIG. 9   FIG. 10
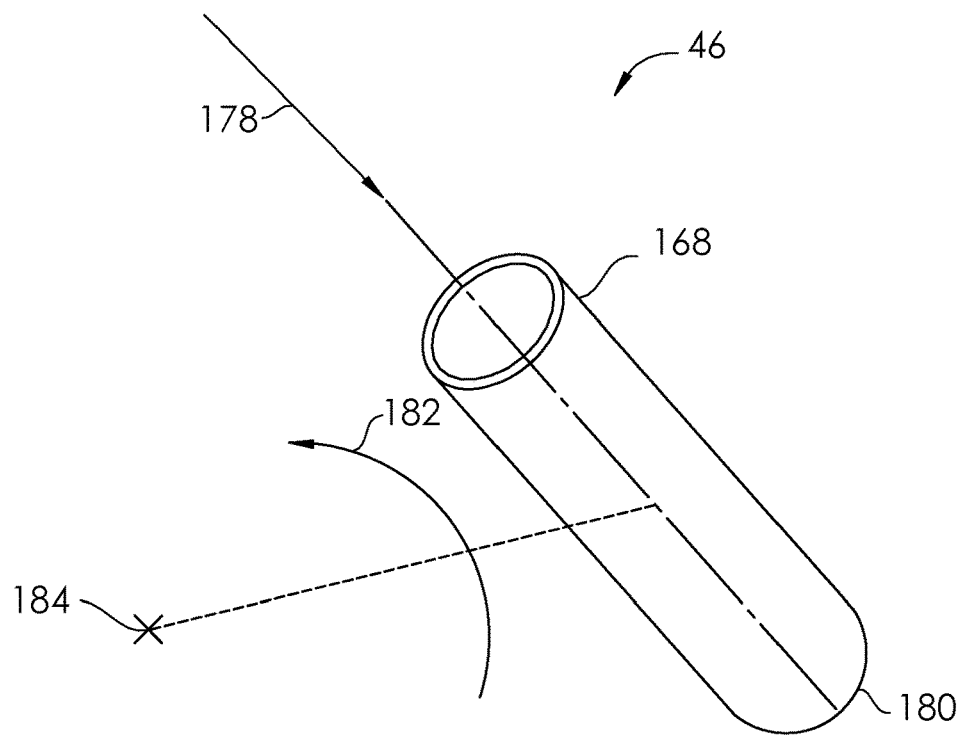
FIG. 8

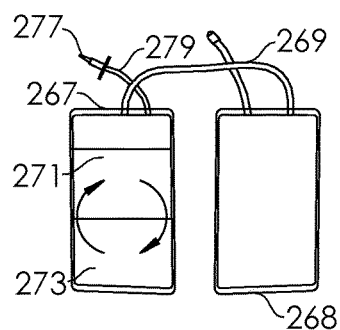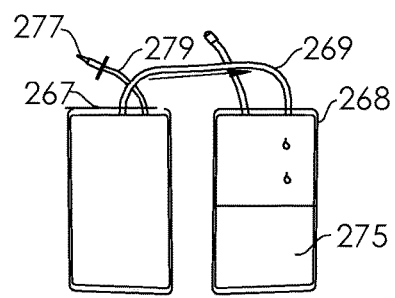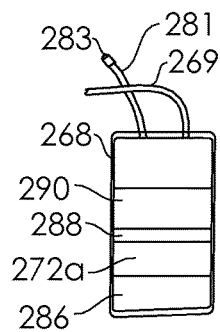
FIG. 12    FIG. 14    FIG. 15
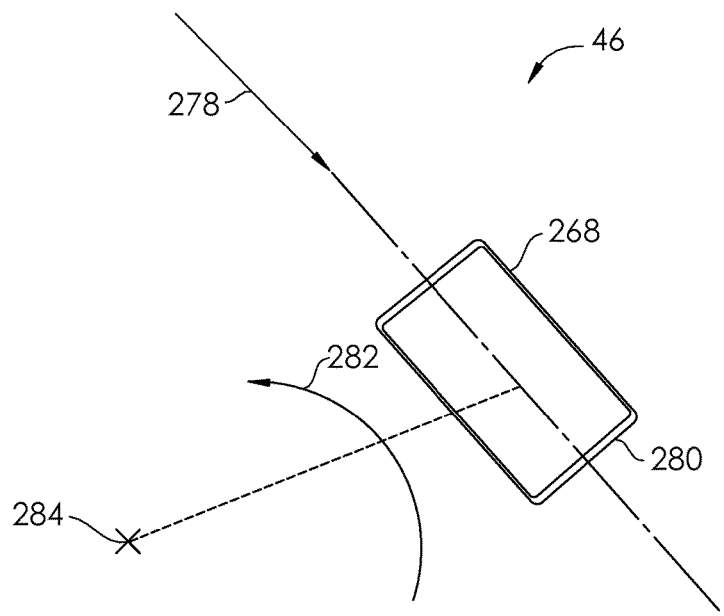
FIG. 13

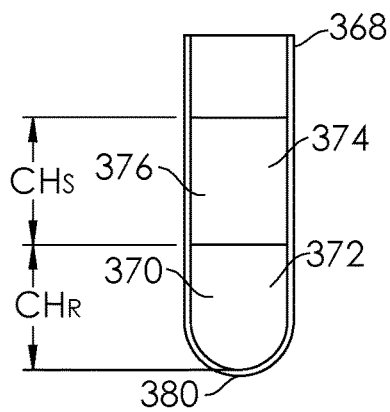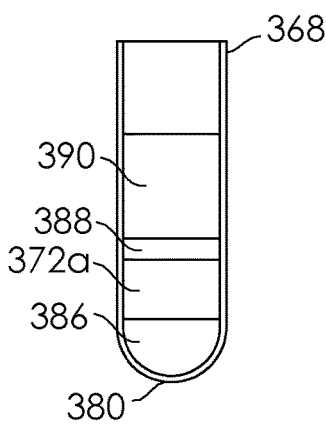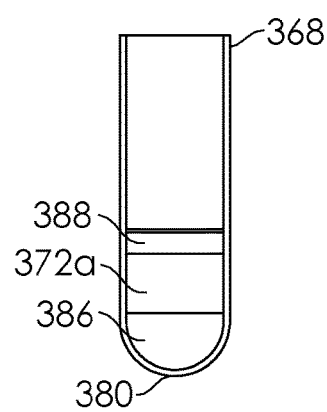
FIG. 17   FIG. 19   FIG. 20
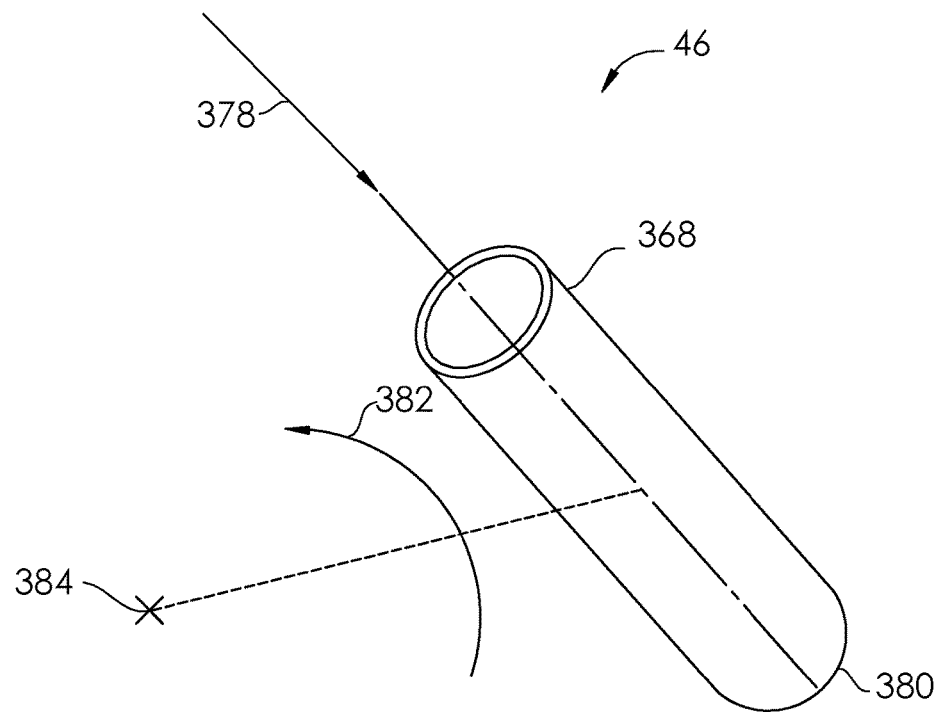
FIG. 18

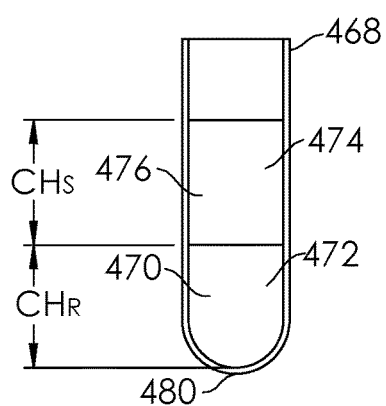
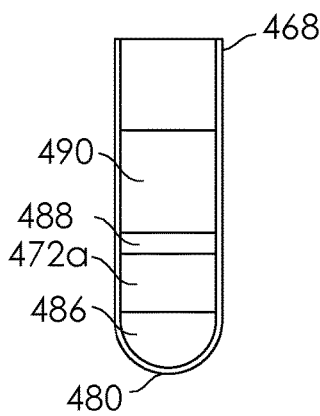
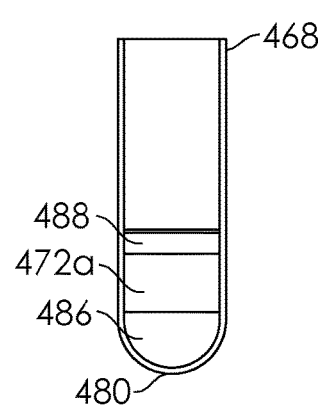
FIG. 22  FIG. 24  FIG. 25
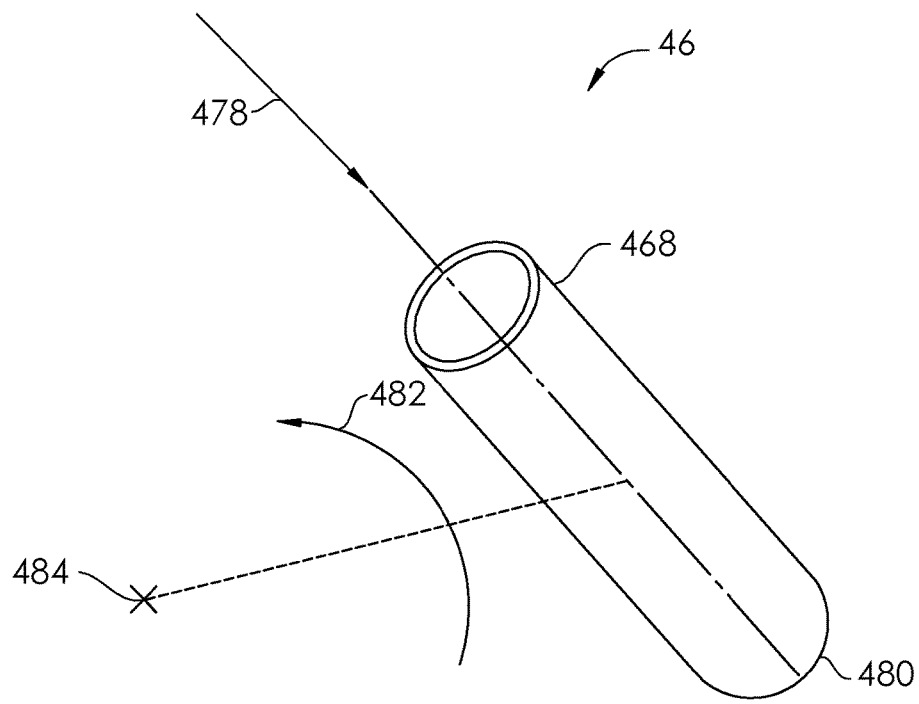
FIG. 23

US 10,213,463 B2

COMPOSITIONS FOR BIOLOGICAL SYSTEMS AND METHODS FOR PREPARING AND USING THE SAME

INCORPORATION BY REFERENCE TO ANY PRIORITY APPLICATIONS

This application is a continuation of U.S. patent application Ser. No. 15/619,467, filed on Jun. 10, 2017, which claims the benefit of priority to U.S. Provisional App. No. 62/349,633, filed on Jun. 13, 2016, both of which are incorporated by reference in their entirety herein for all purposes. Priority is claimed pursuant to 35 U.S.C. § 120 and 35 U.S.C. § 119.

BACKGROUND OF THE INVENTION

The field of the invention generally relates to cellular allograft for tissue redevelopment, including bone redevelopment. The sources of cellular allograft compositions have historically involved adult bone marrow, though recently, placental fluid has been an experimental source.

SUMMARY OF THE INVENTION

In one embodiment, a composition for influencing biological growth includes a solution having a first volume and having low pH fluid base including dextrose, and albumin, wherein the concentration of albumin in the solution is between about 10 mg/ml and about 150 mg/ml.

In another embodiment, a method for performing a therapy in a subject includes providing a composition including a solution having a first volume and including a low pH fluid base including dextrose and albumin, wherein the concentration of albumin in the solution is between about 10 mg/ml and about 150 mg/ml, and implanting within, near, or adjacent tissue of the subject an effective amount of the composition.

In still another embodiment, a composition for influencing biological growth includes a solution having a first volume and including a low pH fluid base including dextrose and a protectant, and wherein the pH of the composition is between 4.1 and 7.2.

In yet another embodiment, a method of making a composition for influencing biological growth configured for implantation within a subject includes obtaining a sample including human umbilical cord blood and having a first volume $V_{UC}$, wherein the human umbilical cord blood includes red blood cells, cells other than red blood cells, and non-cellular material, combining the sample including human umbilical cord blood with a quantity of PrepaCyte-CB or the equivalent having a volume $V_{PC}$, wherein the ratio $V_{UC}/V_{PC}$ is between about 0.60 and about 1.75 such that a supernatant is formed, layering within a container at least a portion of the supernatant over a layer of a reagent configured for isolating mononuclear cells, the at least a portion of the supernatant having a volume $V_S$ and the layer of the reagent having a volume $V_R$, wherein the volume of the layer of the reagent $V_R$ is at least 67% the volume $V_S$ of the at least a portion of the supernatant, placing a sufficient centrifugal force on the contents of the container with a force vector directed toward a closed end of the container to cause at least a new layer substantially including mononuclear cells to form, combining at least some of the layer substantially including mononuclear cells with lactated Ringer's solution or the equivalent to create a mononuclear cell solution, determining the total number of live cells $N_L$ in at least a portion of the mononuclear cell solution, the at least a portion of the mononuclear solution having a volume $V_M$, and adding albumin to the combined composition.

In still another embodiment, a method of making a composition for influencing biological growth configured for implantation within a subject includes obtaining a sample including human umbilical cord blood and having a first volume $V_{UC}$, wherein the human umbilical cord blood includes red blood cells, cells other than red blood cells, and non-cellular material, mixing the sample including human umbilical cord blood with a quantity of PrepaCyte-CB or the equivalent having a volume $V_{PC}$ in a first flexible container, wherein the ratio $V_{UC}/V_{PC}$ is between about 0.60 and about 1.75, allowing the mixture to remain in the first flexible container for at least 20 minutes until a supernatant is formed, forcing at least a portion of the supernatant from the first flexible container into a second flexible container via a conduit linking the first flexible container to the second flexible container, placing a sufficient centrifugal force on the contents of the second flexible container to cause at least a new layer substantially including mononuclear cells to form, combining at least some of the layer substantially including mononuclear cells with a reagent to create a mononuclear cell solution, determining the total number of live cells $N_L$ in at least a portion of the mononuclear cell solution, the at least a portion of the mononuclear solution having a volume $V_M$, and adding albumin to the combined composition.

In yet another embodiment, a method of making a composition for influencing biological growth configured for implantation within a subject includes obtaining a sample including human umbilical cord blood and having a first volume $V_{UC}$, wherein the human umbilical cord blood includes red blood cells, cells other than red blood cells, and non-cellular material, combining the sample including human umbilical cord blood with a quantity of PrepaCyte-CB or the equivalent having a volume $V_{PC}$, wherein the ratio $V_{UC}/V_{PC}$ is between about 0.75 and about 1.25, such that a supernatant is formed, layering within a container at least a portion of the supernatant over a layer of a reagent configured for isolating mononuclear cells, the at least a portion of the supernatant having a column height $CH_S$ and the layer of the reagent having a column height $CH_R$, wherein the column height $CH_R$ is at least 75% the column height $CH_S$ of the at least a portion of the supernatant, placing a sufficient centrifugal force on the contents of the container with a force vector directed toward a closed end of the container to cause at least a new layer substantially including mononuclear cells to form, combining at least some of the layer substantially including mononuclear cells with lactated Ringer's solution or the equivalent to create a mononuclear cell solution, determining the total number of live cells $N_L$ in at least a portion of the mononuclear cell solution, the at least a portion of the mononuclear solution having a volume $V_M$, and adding albumin to the combined composition.

In still another embodiment, a method of making a composition for influencing biological growth configured for implantation within a subject includes obtaining a sample including human umbilical cord blood and having a first volume $V_{UC}$, wherein the human umbilical cord blood includes red blood cells, cells other than red blood cells, and non-cellular material, combining the sample including human umbilical cord blood with a quantity of PrepaCyte-CB or the equivalent having a volume $V_{PC}$, wherein the ratio $V_{UC}/V_{PC}$ is between about 0.75 and about 1.25, such that a supernatant is formed, layering within a container at least a portion of the supernatant over a layer of a reagent configured for isolating mononuclear cells, the at least a portion of the supernatant having a column height $CH_S$ and the layer of the reagent having a column height $CH_R$, wherein the column height $CH_R$ is at least 75% the column height $CH_S$ of the at least a portion of the supernatant, placing a sufficient centrifugal force on the contents of the container with a force vector directed toward a closed end of the container to cause at least a new layer substantially including mononuclear cells to form, combining at least some of the layer substantially including mononuclear cells with lactated Ringer's solution or the equivalent to create a mononuclear cell solution, and determining the total number of live cells $N_L$ in at least a portion of the mononuclear cell solution, the at least a portion of the mononuclear solution having a volume $V_M$.

In yet another embodiment, a method of making a composition for influencing biological growth configured for implantation within a subject includes obtaining a sample including human umbilical cord blood and having a first volume $V_1$, wherein the human umbilical cord blood includes red blood cells, cells other than red blood cells, and non-cellular material, removing at least about 95% of the red blood cells from the sample and removing a substantial amount of the non-cellular material from the sample, such that a resultant pellet from the sample substantially includes cells other than red blood cells, the resultant pellet having a second volume $V_2$, reconstituting at least a portion of the resultant pellet by diluting the at least a portion of the resultant pellet with lactated Ringer's solution, the at least a portion having an initial volume $V_i$ and a resulting diluted portion having a diluted volume $V_{dil}$, such that the ratio $V_{dil}/V_i$ between the diluted volume and the initial volume is between about $0.95 \times V_1/V_2$ and about $1.05 \times V_1/V_2$, layering within a container at least a portion of the resulting diluted portion over a layer of a reagent configured for isolating mononuclear cells, the portion of the resulting diluted portion having a volume $V_3$ and the layer of the reagent having a volume $V_4$, wherein the volume of the layer of the reagent $V_4$ is between about 15% and about 85% of the volume of the portion of the resulting diluted portion $V_3$, placing a sufficient centrifugal force on the container with a force vector directed towards an end of the container including the reagent layer to cause at least a new layer substantially including mononuclear cells to form, combining at least some of the layer of mononuclear cells with lactated Ringer's solution to create a mononuclear cell solution, estimating the number of live cells $N_L$ in at least a portion of the mononuclear cell solution, the at least a portion of the mononuclear solution having a volume $V_5$, adding a volume $V_6$ of Low Molecular Weight Dextran in Dextrose solution to the at least a portion of the mononuclear cell solution, the volume $V_6$ at least partially dependent on the number of live cells $N_L$ in at least a portion of the mononuclear cell solution, adjusting the pH of the combined composition of Low Molecular Weight Dextran in Dextrose solution and mononuclear cell solution if necessary so that it is between 4.1 and 8.5, and adding albumin to the combined composition.

BRIEF DESCRIPTION OF THE DRAWINGS

FIG. 7 illustrates a container having first and second layers placed therein.

FIG. 8 illustrates a general mechanism for applying a centrifugal force on a container.

FIG. 9 illustrates the container of FIG. 7 following the application of a centrifugal force.

FIG. 10 illustrates the container of FIG. 9 after the removal of certain material.

FIG. 12 illustrates first and second flexible containers during an operation.

FIG. 13 illustrates a general mechanism for applying a centrifugal force on the second flexible container of FIG. 12.

FIG. 14 illustrates first and second flexible containers of FIG. 12 during another operation.

FIG. 15 illustrates the second flexible container following the application of a centrifugal force.

FIG. 17 illustrates a container having first and second layers placed therein.

FIG. 18 illustrates a general mechanism for applying a centrifugal force on a container.

FIG. 19 illustrates the container of FIG. 17 following the application of a centrifugal force.

FIG. 20 illustrates the container of FIG. 19 after the removal of certain material.

FIG. 22 illustrates a container having first and second layers placed therein.

FIG. 23 illustrates a general mechanism for applying a centrifugal force on a container.

FIG. 24 illustrates the container of FIG. 22 following the application of a centrifugal force.

FIG. 25 illustrates the container of FIG. 24 after the removal of certain material.

DETAILED DESCRIPTION OF THE ILLUSTRATED EMBODIMENTS

Figure 1:
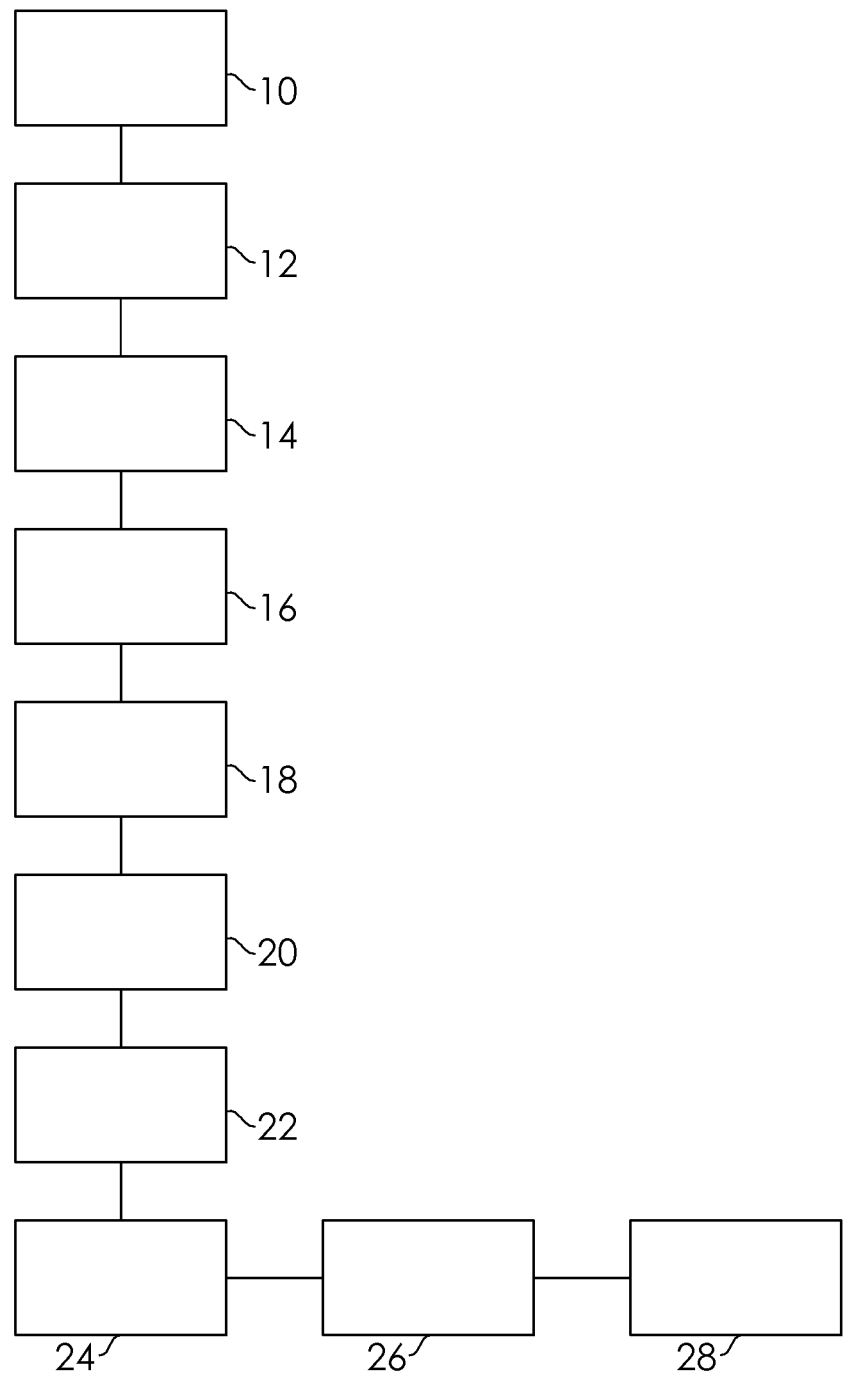
FIG. 1 illustrates a process for forming a composition for implantation within a patient according to a first embodiment.

The present invention relates to a composition of cellular allograft that is derived at least partially from umbilical cord blood, as well as its manufacture and use. Compositions for accelerating or optimizing biological processes or initiating new biological processes may be produced in accordance with the teachings described herein. Cells and growth factors may advantageously be obtained or derived from umbilical cord blood, and may inherently benefit from the advantage that umbilical cord blood includes native cell populations that can support a universal donor application. An inherently increased cellular health may also sustain the benefit of the cellular allograft.

In some embodiments of the compositions, albumin is added. It should be noted that the use of "in some embodiments" herein is intended to mean "in any of the embodiments or combinations of any of the embodiments in which the described element has the possibility or capability of being added." In studies performed by the Applicants, albumin has been shown to increase the viability of cellular components of blood during freezing and thawing procedures that are common during the processing of such compositions. It is thought that albumin may enhance cellular viability post-thaw by acting as a protein stabilizer, preventing the aggregation of proteins in solution as well as decreasing the amount of incorrect protein folding. Correct folding of proteins allows the proteins to, for example, achieve their desired three-dimensional structure. However, misfolded proteins have modified or toxic functionality. Albumin has also been shown to affect the adherence of cells to flasks used during the culturing process (culture flasks). Albumin additionally can enhance the rate of differentiation of umbilical cord blood cells, for example stem cells.

In certain compositions a low, acidic pH, such as a pH between about 4.0 and about 5.0, or about 4.4, may be desirable, such as compositions intended for wound care that includes a cell-free extract. A low pH composition may have a microenvironment that promotes the death and rupture of cells, for example, during freezing or thawing. This death and rupture of cells, or the increase thereof, may result in an increase of soluble extracellular protein factors or bioactive agents, including, but not limited to cytokines or growth factors. These bioactive agents are thought to be a potentially helpful component in the kinetics of wound healing. The kinetics or temporal aspects of wound healing may vary depending on the particular makeup of a composition that is added to tissue of a patient. For example, a composition containing cells that include up to about 70% viable cells may include a larger comparative volume or amount of soluble extracellular factors/bioactive agents than a composition containing cells that include greater than about 95% viable cells. The composition with up to about 70% viable cells may thus cause a more rapid wound healing response than the composition with greater than about 95% viable cells. The use of a relatively low-pH composition as described may thus be utilized in a patient with one or more chronic wounds.

On the other hand, in other compositions, a more alkaline pH, such as a pH between about 7.0 and about 8.0, or about 7.5, may be desirable, such as compositions intended to mediate a biological healing process using viable cells, such as stem cells. Albumin is capable of helping to control the effect of pH on cells, and can thus be incorporated into compositions such as these for this purpose.

The Applicants have also observed that umbilical cord blood cells, when cultured in the presence of albumin, differentiate into several different cell types having varied morphologies. By identifying these particular species of cells, post-differentiation, each particular group of cells may be enhanced to create specialty compositions in each case. For example, one or more particular compositions specially formulated for bone healing or bone growth, one or more particular compositions specially formulated for nerve healing or nerve growth, or other compositions for healing or growth of other types of tissue. After the identification of a cell type, the differentiation of stem cells can be directed toward that particular cell type. With each cell type, certain bioactive agents (cytokines, growth factors, etc.) associated with that cell type may be isolated. These bioactive agents may then be used in particular compositions for specialized purposes. As an example, oncostatin M is a cytokine that sticks to, or binds to extracellular matrix (ECM), and has been identified as a growth factor that affects both bones and nerves. For at least this reason, oncostatin M can be incorporated into bone and/or nerve allograft compositions. As another example, bone morphogenetic proteins (BMP) are growth factors or cytokines that can be incorporated into allograft compositions for use with bone.

A first embodiment of a composition comprises a solution having a first volume and comprising a low pH fluid base comprising dextrose and dextran and also comprising albumin. In some embodiments, the low pH fluid base may comprise LMD (Dextran 40) or an equivalent compound. In some embodiments, the low pH fluid base consists of LMD (Dextran 40). The low pH fluid base of dextrose and dextran, and especially the dextrose component, can act as a proteinaceous protectant by preventing the aggregation of proteins, such as, for example, cytokines. In some embodiments, the albumin in the solution has a concentration of between about 10 mg/ml (milligram per milliliter) and about 150 mg/ml, or between about 10 mg/ml (milligram per milliliter) and about 120 mg/ml. In some embodiments, the albumin in the solution has a concentration of between about 15 mg/ml (milligram per milliliter) and about 30 mg/ml. In some embodiments, the albumin in the solution has a concentration of between about 18 mg/ml (milligram per milliliter) and about 25 mg/ml. In some embodiments, the albumin in the solution has a concentration of about 20 mg/ml. In some embodiments, the albumin in the solution has a concentration of between about 80 mg/ml and about 150 mg/ml, or between about 50 mg/ml and about 150 mg/ml. In some embodiments, the albumin in the solution has a concentration of between about 80 mg/ml and about 120 mg/ml, or between about 50 mg/ml and about 120 mg/ml, or between about 90 mg/ml and about 110 mg/ml. In some embodiments, the albumin in the solution has a concentration of between about 105 mg/ml and about 150 mg/ml, or between about 105 mg/ml and about 120 mg/ml. Together, the low pH fluid base of dextrose and dextran and the albumin act together as a storage agent or protectant (preservative, stabilizer) by maintaining the integrity of proteins obtained from their source (e.g., umbilical cord blood). Another beneficial use of the low pH fluid base of dextrose and dextran is that it provides a relatively low pH, because its baseline pH is lower than physiological pH, thus providing in use an environment that recruits cells that promote wound healing via an increase in signaling proteins. In embodiments in which albumin is added in a powdered form to the low pH fluid base of dextrose and dextran, a cost saving is provided, in comparison to, for example, combining the low pH fluid base of dextrose and dextran and albumin in serum.

A substance such as sodium bicarbonate powder may be added to the solution as needed to control the final pH of the composition. Alternatively, a calcium bicarbonate liquid may be used. For example, in some embodiments, the pH of the composition may be between 4.1 and 7.2. In some embodiments, the pH of the composition may be between 4.1 and 7.4, or in some cases even higher than 7.4. In some embodiments, the pH of the composition may be between 4.1 and 6.2. In some embodiments, the pH of the composition may be between 5.0 and 7.4. In some embodiments, the pH of the composition may be between 5.0 and 6.2. A pH within one of the ranges listed may be achieved in some cases without having to add an additional base such as sodium bicarbonate or calcium bicarbonate, based on the inherent characteristics of the low pH fluid base of dextrose and dextran. In other cases, the additional base may be used in order to achieve a pH within one of the range listed. In certain cases, it may be necessary to use an additional base in order to achieve a pH that is within one of the ranges listed.

In some embodiments, the albumin may be obtained or derived from commercially available human serum. In other embodiments, the albumin may be obtained or derived from donor-derived serum. In some embodiments, the albumin may be obtained or derived from human umbilical cord blood.

In some embodiments, the composition may include progenitor cells. In some embodiments, the composition may comprise stem cells. In some embodiments, the stem cells consist of non-expanded cell populations, for example, not expanded by growth in a Petri dish or growth medium/matrix. The overall makeup of umbilical cord blood cell populations and other factors may provide a broader benefit to a patient. The stem cells may comprise one or more types of stem cells, including, but not limited to, hematopoietic stem cells (HSCs) or mesenchymal stem cells (MSCs). In some embodiments, the stem cells may include viable cells and non-viable cells. In some embodiments, the percentage of viable cells among the stem cells may be greater than 70%. In some embodiments, the percentage of viable cells among the stem cells may be greater than 85%. In some embodiments, the percentage of viable cells among the stem cells may be greater than 95%.

In some embodiments, the composition may comprise live mononuclear cells, which may include, but are not limited to, stem cells or bioactive agents. In some embodiments, the composition comprises between about 2.5 million live mononuclear cells per milliliter (ml) and about 10.2 million live mononuclear cells per milliliter (ml). In some embodiments, the composition comprises between about 9.8 million live mononuclear cells per milliliter (ml) and about 10.2 million live mononuclear cells per milliliter (ml). In some embodiments, the mononuclear cells may be derived from umbilical cord blood of a single donor.

In some embodiments, the composition may comprise one or more bioactive agents, including but not limited to cytokines or growth factors. The bioactive agents may include any of the following: chemokines, including macrophage inflammatory protein alpha (MIP-1α), macrophage inflammatory protein beta (MIP-1β), and interferon gamma-induced protein 10 (IP-10), interleukins, including interleukin 1 Beta (IL-1β), interleukin 2 (IL-2), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), and interleukin 13 (IL-13), interferons, including interferon alpha (INFα), lymphokines, granulocyte macrophage colony stimulating factor (GM-CSF), stem cell factor (KL), and tumor necrosis factor alpha (TNF-α). The bioactive agents may also include any of the following: vascular endothelial growth factor (VEGF), nerve growth factor, platelet-derived growth factor (PDGF), fibroblast growth factors (FGF), including fibroblast growth factor 2 (FGF-2), epidermal growth factor (EGF), keratinocyte growth factor, transforming growth factor (TGF), insulin-like growth factor, des(1-3)-IGF-I (brain IGF-I), neurotrophin-3 (NT-3) and brain-derived neurotrophic factor (BDNF).

Other bioactive agents that may be incorporated into the composition may include one or more of the following: transforming growth factor Beta 1 (TGF-β1), transforming growth factor Alpha 1 (TGF-α1), interleukin 16 (IL-16), platelet factor 4 (PF4), interferon gamma (IFNγ), hepatocyte growth factor (HGF), insulin growth factor (IGF-1), fas ligand (Fas-L), monocyte chemoattractant protein 2 (MCP-2), monocyte chemoattractant protein 3 (MCP-3), monocyte chemoattractant protein 4 (MCP-4), macrophage derived chemokine (MDC), platelet factor 4 (PF-4), thrombopoietin (TPO), insulin-like growth factor 1 (IGF-1), and insulin-like growth factor binding protein-3 (IGFBP-3).

Other bioactive agents that may be incorporated into the composition may include one or more of the following: interleukin 15 (IL-15), interleukin 17 (IL-17), interleukin 18 (IL-18), interleukin 21 (IL-21), interleukin 22 (IL-22), interleukin 23 (IL-23), interleukin 27 (IL-27), interleukin 31 (IL-31), eotaxin, CXC ligand 1 (GROα), interleukin 1 receptor antagonist (IL-1RA), interleukin 1 alpha (IL-1α), leukemia inhibitory factor (LIF), placental growth factor (PLGF), chemokine ligand 5 (RANTES), stem cell factor (SCF), stromal cell derived factor (SDF1α), and tumor necrosis factor (TNF β). Each Interleukin category may comprise one or more members within a category or family. For example, within the Interleukin 17 (IL-17) category, one of several species may be chosen, such as IL-17A, IL-17B, IL-17C, IL-17D, IL-17E, or others. When IL-17 is generically denoted, it is intended to encompass any one or more of these different species.

In some embodiments, the composition may include albumin and one or more bioactive agents, wherein the albumin is derived from umbilical cord blood of a first donor, and the one or more bioactive agents are derived from at least a second donor. The one or more bioactive agents may be taken or derived from commercially available human albumin and/or commercially available human albumin serum. In some embodiments, the composition may include albumin and one or more bioactive agents, wherein the albumin and the one or more bioactive agents are derived from umbilical cord blood of a single donor.

In some embodiments, the composition may be produced such that it does not comprise dimethyl sulfoxide (DMSO) to avoid any potential harmful effects that DMSO may have, such as inducing allergic reactions in a subject. However, in some embodiments, DMSO may still be used, for example, as a cryoprotectant, as a replacement for Dextran, or in combination with Dextran. An alternative cryoprotectant or cryopreservative that may be substituted for Dextran and/or for DMSO, is CryoGold™, supplied by System Biosciences, Inc. of Palo Alto, Calif., USA. Glycerol is another alternative cryoprotectant or cryopreservative that may be substituted.

Figure 2:
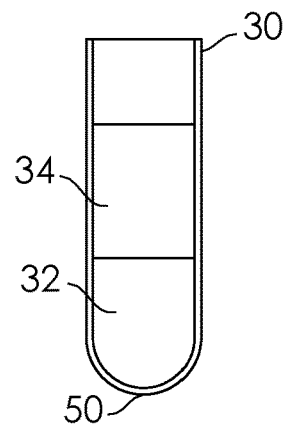
FIG. 2 illustrates a container having first and second layers placed therein.

A method of producing compositions such as the embodiments described herein is described according to a first embodiment. In step 10 of FIG. 1, a sample comprising human umbilical cord blood and having a first volume $V_1$ is obtained. The human umbilical cord blood typically includes red blood cells, cells other than red blood cells, and non-cellular material. In step 12, at least about 95% of the red blood cells are removed from the sample and a substantial about of the non-cellular material is removed from the sample. Step 12 produces a pellet substantially comprising cells other than red blood cells. The pellet has a second volume $V_2$. In some embodiments, at least about 98% of the red blood cells are removed from the sample. In some embodiments, at least about 99% of the red blood cells are removed from the sample. In some embodiments, at least about 95% (by volume) or the non-cellular material is removed from the sample. In some embodiments, the removal of red blood cells and/or non-cellular material may comprise combining the human umbilical cord blood with PrepaCyte®-CB solution, Bio-E, LLC, Bloomington, Minn., or an equivalent aggregation agent or sedimentation agent. In some embodiments, the removal of red blood cells and/or non-cellular material may comprise placing the human umbilical cord blood in a container within a centrifuge, and operating the centrifuge. This may occur after combining the human umbilical cord blood with PrepaCyte-CB solution, or an equivalent aggregation agent or sedimentation agent. In step 14, at least a portion of the pellet is reconstituted by diluting it with lactated Ringer's solution. The at least a portion of pellet has an initial volume $V_i$, and the resulting diluted portion has a diluted volume $V_{dil}$. In some embodiments, a ratio $V_{dil}/V_i$ between the diluted volume and the initial volume is between about $0.95 \times V_1/V_2$ and about $1.05 \times V_1/V_2$. In step 16, a container 30 (FIG. 2), which may comprise a tube configured for placement within a centrifuge, is filled with two layers. As shown in FIG. 2, a first layer 32 comprises a reagent that is configured for isolating mononuclear cells. In some embodiments, the reagent comprises Ficoll-Paque® Centrifugation Media, GE Healthcare Bio-Sciences AB, Uppsala, Sweden, or equivalent media. In some embodiments, the reagent comprises Ficoll-Paque® PLUS Centrifugation Media. In some embodiments, the reagent comprises Ficoll-Paque® PREMIUM Centrifugation Media. In some embodiments, the reagent has a density of between about 1.0 grams/ml and about 1.3 grams/ml. In some embodiments, the reagent has a density of between about 1.07 grams/ml and about 1.09 grams/ml. In some embodiments, the reagent has a density of between about 1.073 grams/ml and about 1.084 grams/ml. A second layer 34 is placed over the first layer 32. The second layer 34 comprises at least a portion of the resulting diluted portion from step 14. The first layer 32 and second layer 34 are placed in the container 30, such that a volume $V_3$ of the second layer 34 is placed over a volume $V_4$ of the first layer 32, such that volume $V_4$ is between about 15% and about 85% of $V_3$. In some embodiments, volume $V_4$ is between about 45% and about 55% of $V_3$. In some embodiments, volume $V_4$ is between about 75% and about 85% of $V_3$. In some embodiments, volume $V_4$ is about 50% of $V_3$.

Figure 4:
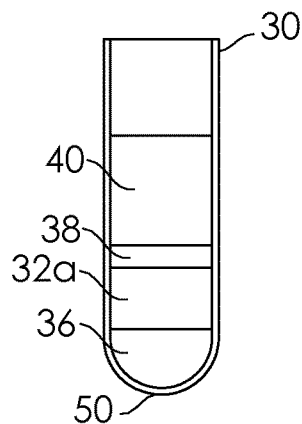
FIG. 4 illustrates the container of FIG. 2 following the application of a centrifugal force.
Figure 3:
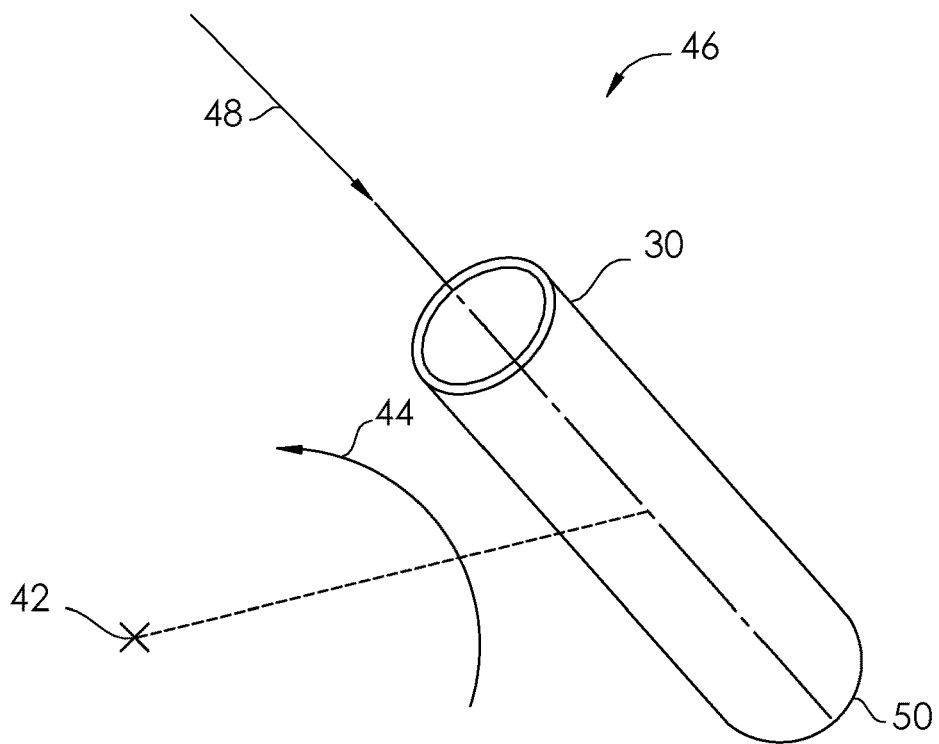
FIG. 3 illustrates a general mechanism for applying a centrifugal force on a container.

In step 18, a sufficient centrifugal force component 48 is placed on the container 30 (FIG. 3) and its contents (e.g., first layer 32 and second layer 34), with the centrifugal force component 48 directed toward a closed container end 50, to cause layering as shown in FIG. 4 to form. FIG. 3 illustrates the basic mechanics of a centrifuge 46 which spins the container 30 in a circular path 44 around a center point 42. In FIG. 4, a layer 36 comprises granulocytes and erythrocytes, and has migrated below a layer 32a containing the reagent which is configured for isolating mononuclear cells, and which remains from the first layer 32 of FIG. 2. Layer 38 substantially comprises mononuclear cells, and layer 40 substantially comprises plasma and platelets. In some embodiments, step 18 may be performed using a centrifuge which places at least about 350 times the acceleration due to gravity on the container 30 and its contents. In some embodiments, step 18 may be performed using a centrifuge which places at least about 400 times the acceleration due to gravity on the container 30 and its contents. In some embodiments, step 18 may be performed using a centrifuge which places at least about 450 times the acceleration due to gravity on the container 30 and its contents. In some embodiments, the centrifuge may be run between about 5 minutes and about 30 minutes to achieve the desired result.

In addition to controlling the amount of centrifugal force on the contents and/or the amount of time that the centrifuge is operated, a user may also choose to control the ramp up and ramp down of the centrifuge; in other words, the time required to reach the chosen centrifugal force from a stopped condition, and the time required to reach a stopped condition from the nominally chosen centrifugal force. In a traditional centrifuge, this corresponds to the speeding up of the rotational speed (e.g., RPM) until a desired constant operation rate is reached, and the slowing down of the rotational speed (from a desired constant operation rate) to a stopped condition. The control of one or both of these two elements can be used to further optimize the effectiveness of the centrifugation. The time to ramp up to a desired centrifugal force from substantially zero centrifugal force may be between about 30 seconds and about 15 minutes, or between about one minute and about five minutes. The time to ramp down from a desired centrifugal force to substantially zero centrifugal force may be between about 30 seconds and about 20 minutes, or between about one minute and about 10 minutes.

Figure 5:
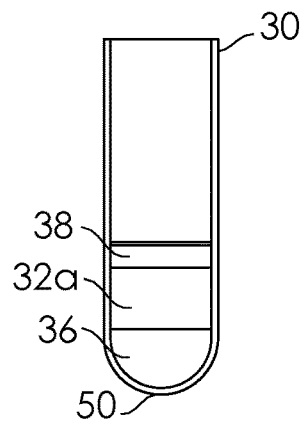
FIG. 5 illustrates the container of FIG. 4 after the removal of certain material.

In step 20 mononuclear cells from the mononuclear cell layer 38 are removed from the container 30 and are combined with lactated Ringer's solution, to create a mononuclear cell solution. Prior to the removal of the mononuclear cells from the container 30, the layer 40 may be first removed (FIG. 5), thus making it easier to remove the layer 38. Care can be taken so that the layer 38 is not disturbed when removing the layer 40, for example, by use of a sterile pipette. In step 22, the mononuclear cells are actively (though gently) mixed with the lactated Ringer's solution. The mononuclear cells may also be washed one, two, or more times with lactated Ringer's solution. In some embodiments, the mononuclear cell solution substantially comprises non-expanded cell populations. In some embodiments, the mononuclear cell solution comprises non-pooled cell populations. It should be noted that the layer 40 is substantially removed prior to removing the layer 38 to minimize any unnecessary contamination by platelets or plasma proteins. It should also be noted that the layer 32a is left substantially undisturbed when removing the layer 38, thus minimizing any unnecessary contamination by granulocytes.

In step 22, a volume $V_5$ of either a portion of the mononuclear cell solution or substantially all of the mononuclear cell solution is used in order to estimate the number $N_L$ of live cells in the volume $V_5$. In some embodiments, the estimating is done by performing a CD34+ count. In some embodiments, the estimating is done by performing a Total Nucleated Cell (TNC) count. In some embodiments, the estimating is done at least in part with an automated cell counter. Alternative methods may be used for performing the cell count, including: a hemtocytometer following trypan blue staining, an ATP test, Calcein AM, a clonogenic assay, an ethidium homodimer assay, Evans blue, fluorescein diacetate hydrolysis/propidium iodide staining (FDA/PI staining), flow cytometry, formazan-based-assays (MTT/XTT), green fluorescent protein, lactate dehydrogenase (LDH), methyl violet, propidium iodide DNA stain (to differentiate necrotic, apoptotic, and normal cells), resazurin, trypan blue which only crosses cell membranes of dead cells, or TUNEL assay. At the end of step 22 substantially all of the lactated Ringer's solution may be removed from the volume $V_5$. In step 24, based at least partially upon the estimated number $N_L$ of live cells, a calculated, estimated or determined volume $V_6$ of Low Molecular Weight Dextran in Dextrose solution is added to the volume $V_5$ of the at least a portion of the mononuclear cell solution. In some embodiments, the calculation, estimation or determination of the volume $V_6$ may be at least partially based on the assumption that approximately 75% of cells in the at least a portion mononuclear cell solution will be viable following freezing and thawing. In some embodiments, the calculation, estimation or determination of the volume $V_6$ may be at least partially based on an intended live cell concentration of between about 2.5 million live cells and about 10.2 million live cells per milliliter. In some embodiments, the cells may be stored cryogenically. In some embodiments, the cryogenic storage is below about −60° C. In some embodiments, the cryogenic storage is below about −80° C. In some embodiments, the calculation, estimation or determination of the volume $V_6$ may be at least partially based on an intended live cell concentration of between about 2.5 million live cells and about 10.2 million live cells per milliliter, and may assume that this live cell concentration will occur after adding albumin to the combined composition and cryogenically storing the combined composition. In some embodiments, the calculation, estimation or determination of the volume $V_6$ may be at least partially based on an intended live cell concentration of between about 9.8 million live cells and about 10.2 million live cells per milliliter. In some embodiments, the Low Molecular Weight Dextran in Dextrose may comprise LMD (Dextran 40). In some embodiments, the volume $V_6$ added corresponds to the equation $$V_6 = K \times N_L,$$

where K is between about $7.35 \times 10^{-8}$ ml/cell and about $3.00 \times 10^{-7}$ ml/cell, and where $N_L$ is the number of live cells in a 20 ml portion of the mononuclear cell solution.

In some embodiments, the volume $V_6$ added corresponds to the equation $$V_6 = K \times N_L,$$

where K is between about $7.35 \times 10^{-8}$ ml/cell and about $7.50 \times 10^{-8}$ ml/cell, and where $N_L$ is the number of live cells in a 20 ml portion of the mononuclear cell solution.

In step 26, the pH of the combined composition of the mononuclear cell solution and Low Molecular Weight Dextran in Dextrose solution may be adjusted if needed, in order to produce a pH within a desired range. In some embodiments, the pH is adjusted by adding a sodium bicarbonate, such as sodium bicarbonate powder. In some embodiments, the pH is adjusted by adding a calcium bicarbonate, such as calcium bicarbonate liquid. In some embodiments, the pH is adjusted to or maintained at between 4.1 and 8.5. In some embodiments, the pH is adjusted to or maintained at between 4.1 and 7.2. In some embodiments, the pH is adjusted to or maintained at between 4.1 and 6.2. In some embodiments, the pH is adjusted to or maintained at between 5.0 and 7.4. In some embodiments, the pH is adjusted to or maintained at between 5.0 and 7.2. In some embodiments, the pH is adjusted to or maintained at between 5.0 and 6.2. In step 28, albumin is added to the combined composition. In some embodiments, between about 10 mg and about 150 mg of albumin may be added per one milliliter of the combined composition. In some embodiments, between about 15 mg and about 30 mg of albumin may be added per one milliliter of the combined composition. In some embodiments, between about 18 mg and about 25 mg of albumin may be added per one milliliter of the combined composition. In some embodiments, about 20 mg of albumin may be added per one milliliter of the combined composition.

In some embodiments, the mononuclear cell solution comprises stem cells. In some embodiments, the stem cells comprise hemapoietic stem cells (HSC). In some embodiments, the stem cells comprise mesenchymal stem cells (MSC).

In some embodiments, one or more bioactive agents may be added to the composition. The one or more bioactive agents may include cytokines or growth factors, and may be derived from human umbilical cord blood. In some embodiments, the one or more bioactive agents may be obtained or derived from the same sample comprising human umbilical cord blood that is described in step 10. In some embodiments, the one or more bioactive agents may be obtained or derived from human umbilical cord blood that is not the sample comprising human umbilical cord blood that is described in step 10. In some embodiments, the one or more bioactive agents may be obtained or derived from human umbilical cord blood that is from a different donor than the sample comprising human umbilical cord blood that is described in step 10. In some embodiments, the one or more bioactive agents are obtained or derived from commercially available human albumin or commercially available human albumin serum.

In some embodiments, the one or more bioactive agents may include but are not limited to cytokines or growth factors. The bioactive agents may include any of the following: chemokines, including macrophage inflammatory protein alpha (MIP-1α), macrophage inflammatory protein beta (MIP-1β), and interferon gamma-induced protein 10 (IP-10), interleukins, including interleukin 1 Beta (IL-1β), interleukin 2 (IL-2), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), and interleukin 13 (IL-13), interferons, including interferon alpha (INFα), lymphokines, granulocyte macrophage colony stimulating factor (GM-CSF), stem cell factor (KL), and tumor necrosis factor alpha (TNF-α). The bioactive agents may also include any of the following: vascular endothelial growth factor (VEGF), nerve growth factor, platelet-derived growth factor (PDGF), fibroblast growth factors (FGF), including fibroblast growth factor 2 (FGF-2), epidermal growth factor (EGF), keratinocyte growth factor, transforming growth factor (TGF), insulin-like growth factor, des(1-3)-IGF-I (brain IGF-I), neurotrophin-3 (NT-3) and brain-derived neurotrophic factor (BDNF).

In some embodiments, dimethyl sulfoxide (DMSO) is not added into the composition in any of the steps, thus leaving the composition substantially DMSO-free, and to avoid any potential harmful effects that DMSO may have. The combined composition may then be cryogenically stored, for example, in cryogenic vials in an ultra-low freezer. The cryogenic storage may be controlled at a temperature below −60° C., or below −80° C.

Figure 6:
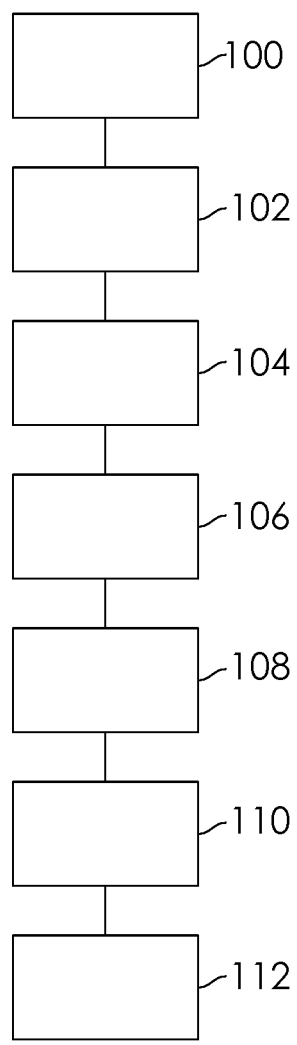
FIG. 6 illustrates a process for forming a composition for implantation within a patient according to a second embodiment.

A method of producing compositions such as the embodiments described herein is described according to a second embodiment. In step 100 of FIG. 6, a sample comprising human umbilical cord blood and having a first volume $V_{UC}$ is obtained. The human umbilical cord blood typically includes red blood cells, cells other than red blood cells, and non-cellular material. In step 102, the sample comprising human umbilical cord blood is combined with a volume Vpc of PrepaCyte®-CB solution, Bio-E, LLC, Bloomington, Minn., or an equivalent aggregation agent or sedimentation agent. Either or both of the volumes $V_{UC}$ and $V_{PC}$ may be selected such that the ratio $V_{UC}/V_{PC}$ is between about 0.60 and about 1.75. In some embodiments, the ratio $V_{UC}/V_{PC}$ is between about 0.75 and about 1.25. In some embodiments, the ratio $V_{UC}/V_{PC}$ is between about 0.60 and about 1.10. In some embodiments, the ratio $V_{UC}/V_{PC}$ is between about 1.25 and about 1.75. The combined volumes $V_{UC}$ and $V_{PC}$ are allowed to stand undisturbed for at least about 20 minutes, or at least about 30 minutes, until a supernatant is formed, or until at least two distinct layers are formed. In step 104, a container 168 configured to be subjected to a centrifugal force (e.g., a centrifuge tube) is partially filled with a reagent 170 (FIG. 7) which is configured for isolating mononuclear cells, the reagent 170 having a volume $V_R$. In some embodiments, the reagent 170 comprises Ficoll-Paque® Centrifugation Media, GE Healthcare Bio-Sciences AB, Uppsala, Sweden, or equivalent media. In some embodiments, the reagent 170 comprises Ficoll-Paque® PLUS Centrifugation Media. In some embodiments, the reagent 170 comprises Ficoll-Paque® PREMIUM Centrifugation Media. In some embodiments, the reagent 170 has a density of between about 1.0 grams/ml and about 1.3 grams/ml. In some embodiments, the reagent 170 has a density of between about 1.07 grams/ml and about 1.09 grams/ml. In some embodiments, the reagent 170 has a density of between about 1.073 grams/ml and about 1.084 grams/ml. The volume $V_R$ of the reagent 170 represents a first layer 172 (e.g., bottom layer) in the container 168. Further, as part of step 104, a second layer 174 comprising a volume $V_S$ of the supernatant 176 produced in step 102 is layered over first layer 172 in the container 168, as shown in FIG. 7. The volume $V_R$ of the layer 172 of the reagent 170 is at least 67% of the volume $V_S$ of the layer 174 of the supernatant 176. In some embodiments, the volume $V_R$ of the layer 172 of the reagent 170 is at least 75% of the volume $V_S$ of the layer 174 of the supernatant 176. In some embodiments, the volume $V_R$ of the layer 172 of the reagent 170 is at least 85% of the volume $V_S$ of the layer 174 of the supernatant 176. In some embodiments, the volume $V_R$ of the layer 172 of the reagent 170 is between about 30% and about 135% of the volume $V_S$ of the layer 174 of the supernatant 176. In some embodiments, the volume $V_R$ of the layer 172 of the reagent 170 is between about 50% and about 100% of the volume $V_S$ of the layer 174 of the supernatant 176. In some embodiments, the volume $V_R$ of the layer 172 of the reagent 170 is between about 75% and about 100% of the volume $V_S$ of the layer 174 of the supernatant 176. The second layer 174 should be added over the first layer 172 in a slow or at least gentle or non-disruptive manner (e.g., slow speed pipetting) if a distinct interface between the two layers 172, 174 is initially desired.

In step 106, a sufficient centrifugal force component 178 is placed on the container 168 (FIG. 8) and its contents (e.g., first layer 172 and second layer 174), with the centrifugal force component 178 directed toward a closed container end 180, to cause layering as shown in FIG. 9 to form. FIG. 8 illustrates the basic mechanics of a centrifuge 46 which spins the container 168 in a circular path 182 around a center point 184. The container 168 may, for example, be carefully placed within the centrifuge 46 in an appropriate location for spinning. In FIG. 9, a layer 186 comprises granulocytes and erythrocytes, and has migrated below a layer 172a containing the reagent 170, and which remains from the first layer 172 of FIG. 7. Layer 188 substantially comprises mononuclear cells, and layer 190 substantially comprises plasma and platelets. In some embodiments, step 106 may be performed using a centrifuge which places at least about 350 times the acceleration due to gravity on the container 168 and its contents. In some embodiments, step 106 may be performed using a centrifuge which places at least about 400 times the acceleration due to gravity on the container 168 and its contents. In some embodiments, step 106 may be performed using a centrifuge which places at least about 450 times the acceleration due to gravity on the container 168 and its contents. In some embodiments, step 106 may be performed using a centrifuge which places at least about 600 times the acceleration due to gravity on the container 168 and its contents. In some embodiments, step 106 may be performed using a centrifuge which places at least about 800 times the acceleration due to gravity on the container 168 and its contents. In some embodiments, step 106 may be performed using a centrifuge which places at least about 1,400 times the acceleration due to gravity on the container 168 and its contents. In some embodiments, the centrifuge may be run between about 5 minutes and about 30 minutes to achieve the desired result.

In addition to controlling the amount of centrifugal force on the contents and/or the amount of time that the centrifuge is operated, a user may also choose to control the ramp up and ramp down of the centrifuge; in other words, the time required to reach the chosen centrifugal force from a stopped condition, and the time required to reach a stopped condition from the nominally chosen centrifugal force. In a traditional centrifuge, this corresponds to the speeding up of the rotational speed (e.g., RPM) until a desired constant operation rate is reached, and the slowing down of the rotational speed (from a desired constant operation rate) to a stopped condition. The control of one or both of these two elements can be used to further optimize the effectiveness of the centrifugation. The time to ramp up to a desired centrifugal force from substantially zero centrifugal force may be between about 30 seconds and about 15 minutes, or between about one minute and about five minutes. The time to ramp down from a desired centrifugal force to substantially zero centrifugal force may be between about 30 seconds and about 20 minutes, or between about one minute and about 10 minutes.

In step 108, mononuclear cells from the mononuclear cell layer 188 are removed from the container 168 and are combined with lactated Ringer's solution, to create a mononuclear cell solution. Prior to the removal of the mononuclear cells from the container 168, the layer 190 may be first removed (FIG. 10), thus making it easier to remove the layer 188. Care can be taken so that the layer 188 is not disturbed when removing the layer 190, for example, by use of a sterile pipette. In step 108, the mononuclear cells from the mononuclear cell layer 188 are actively (though gently) mixed with the lactated Ringer's solution. The mononuclear cells may also be washed one, two, or more times with lactated Ringer's solution. In some embodiments, the mononuclear cell solution substantially comprises non-expanded cell populations. In some embodiments, the mononuclear cell solution comprises non-pooled cell populations. It should be noted that the layer 190 is substantially removed prior to removing the mononuclear cells from the layer 188 to minimize any unnecessary contamination by platelets or plasma proteins. It should also be noted that the layer 172a is left substantially undisturbed when removing the layer 188, thus minimizing any unnecessary contamination by the granulocytes in layer 186.

In step 110, a volume $V_M$ of either a portion of the mononuclear cell solution or substantially all of the mononuclear cell solution is used in order to estimate the number $N_L$ of live cells in the volume $V_M$. In some embodiments, the estimating is done by performing a CD34+ count. In some embodiments, the estimating is done by performing a Total Nucleated Cell (TNC) count. In some embodiments, the estimating is done at least in part with an automated cell counter. Alternative methods may be used for performing the cell count, including: a hemtocytometer following trypan blue staining, an ATP test, Calcein AM, a clonogenic assay, an ethidium homodimer assay, Evans blue, fluorescein diacetate hydrolysis/propidium iodide staining (FDA/PI staining), flow cytometry, formazan-based-assays (MTT/XTT), green fluorescent protein, lactate dehydrogenase (LDH), methyl violet, propidium iodide DNA stain (to differentiate necrotic, apoptotic, and normal cells), resazurin, trypan blue which only crosses cell membranes of dead cells, or TUNEL assay. At the end of step 110 substantially all of the lactated Ringer's solution may be removed from the volume $V_M$.

In step 112, albumin is added to the combined composition. In some embodiments, between about 10 mg and about 150 mg of albumin may be added per one milliliter of the combined composition. In some embodiments, between about 10 mg and about 120 mg of albumin may be added per one milliliter of the combined composition. In some embodiments, between about 50 mg and about 150 mg of albumin may be added per one milliliter of the combined composition. In some embodiments, between about 50 mg and about 120 mg of albumin may be added per one milliliter of the combined composition. In some embodiments, between about 80 mg and about 150 mg of albumin may be added per one milliliter of the combined composition. In some embodiments, between about 80 mg and about 120 mg of albumin may be added per one milliliter of the combined composition. In some embodiments, between about 105 mg and about 150 mg of albumin may be added per one milliliter of the combined composition. In some embodiments, between about 105 mg and about 120 mg of albumin may be added per one milliliter of the combined composition. In some embodiments, between about 15 mg and about 30 mg of albumin may be added per one milliliter of the combined composition. In some embodiments, between about 18 mg and about 25 mg of albumin may be added per one milliliter of the combined composition. In some embodiments, about 20 mg of albumin may be added per one milliliter of the combined composition.

In some embodiments, Low Molecular Weight Dextran in Dextrose solution is added to the volume $V_M$ of the at least a portion of the mononuclear cell solution during or prior to the addition of albumin. In some embodiments, the amount of Low Molecular Weight Dextran in Dextrose solution is based at least partially upon the estimated number $N_L$ of live cells, a calculated, estimated or determined. In some embodiments, the calculation, estimation or determination of the volume $V_{DD}$ pf the Low Molecular Weight Dextran in Dextrose solution added may be at least partially based on the assumption that approximately 75% of cells in the at least a portion mononuclear cell solution will be viable following freezing and thawing. In some embodiments, the calculation, estimation or determination of the volume $V_{DD}$ may be at least partially based on an intended live cell concentration of between about 100,000 live cells and about 75 million live cells per milliliter. In some embodiments, the calculation, estimation or determination of the volume $V_{DD}$ may be at least partially based on an intended live cell concentration of between about 750,000 live cells and about 30 million live cells per milliliter. In some embodiments, the cells may be stored cryogenically. In some embodiments, the calculation, estimation or determination of the volume $V_{DD}$ may be at least partially based on an intended live cell concentration of between about 10 million live cells and about 30 million live cells per milliliter. In some embodiments, the calculation, estimation or determination of the volume $V_{DD}$ may be at least partially based on an intended live cell concentration of between about 10 million live cells and about 20 million live cells per milliliter. In some embodiments, the cryogenic storage is below about −60° C. In some embodiments, the cryogenic storage is below about −80° C.

In some embodiments, the pH of the combined composition may be adjusted if needed, in order to produce a pH within a desired range. In some embodiments, the pH is adjusted by adding a sodium bicarbonate, such as sodium bicarbonate powder. In some embodiments, the pH is adjusted by adding a calcium bicarbonate, such as calcium bicarbonate solution. In some embodiments, the pH is adjusted to or maintained at between 4.1 and 8.5. In some embodiments, the pH is adjusted to or maintained at between 4.1 and 7.2. In some embodiments, the pH is adjusted to or maintained at between 4.1 and 6.2. In some embodiments, the pH is adjusted to or maintained at between 5.0 and 7.4. In some embodiments, the pH is adjusted to or maintained at between 5.0 and 7.2. In some embodiments, the pH is adjusted to or maintained at between 5.0 and 6.2.

In some embodiments, the mononuclear cell solution comprises stem cells. In some embodiments, the stem cells comprise hemapoietic stem cells (HSC). In some embodiments, the stem cells comprise mesenchymal stem cells (MSC).

In some embodiments, one or more bioactive agents may be added to the composition. The one or more bioactive agents may include cytokines or growth factors, and may be derived from human umbilical cord blood. In some embodiments, the one or more bioactive agents may be obtained or derived from the same sample comprising human umbilical cord blood that is described in step 100. In some embodiments, the one or more bioactive agents may be obtained or derived from human umbilical cord blood that is not the sample comprising human umbilical cord blood that is described in step 100. In some embodiments, the one or more bioactive agents may be obtained or derived from human umbilical cord blood that is from a different donor than the sample comprising human umbilical cord blood that is described in step 100. In some embodiments, the one or more bioactive agents are obtained or derived from commercially available human albumin or commercially available human albumin serum.

In some embodiments, the one or more bioactive agents may include but are not limited to cytokines or growth factors. The bioactive agents may include any of the following: chemokines, including macrophage inflammatory protein alpha (MIP-1α), macrophage inflammatory protein beta (MIP-1β), interferon gamma-induced protein 10 (IP-10), interleukins, including interleukin 1 Beta (IL-1β), interleukin 2 (IL-2), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 12 (IL-12), interleukin 13 (IL-13), interleukin 15 (IL-15), interleukin 17 (IL-17), interleukin 18 (IL-18), interleukin 21 (IL-21), interleukin 22 (IL-22), interleukin 23 (IL-23), interleukin 27 (IL-27), interleukin 31 (IL-31), interferons, including interferon alpha (INFα), a lymphokine, granulocyte macrophage colony stimulating factor (GM-CSF), stem cell factor (KL), tumor necrosis factor alpha (TNF-α), vascular endothelial growth factor (VEGF), nerve growth factor, platelet-derived growth factor (PDGF), fibroblast growth factor 2 (FGF-2), epidermal growth factor (EGF), keratinocyte growth factor, transforming growth factor (TGF), insulin-like growth factor, des(1-3)-IGF-I (brain IGF-I), neurotrophin-3 (NT-3), brain-derived neurotrophic factor (BDNF), eotaxin, CXC ligand 1 (GROα), interleukin 1 receptor antagonist (IL-1RA), interleukin 1 alpha (IL-1α), leukemia inhibitory factor (LIF), placental growth factor (PLGF), chemokine ligand 5 (RANTES), stem cell factor (SCF), stromal cell derived factor (SDF1α), and tumor necrosis factor (TNF β).

In some embodiments, dimethyl sulfoxide (DMSO) is not added into the composition in any of the steps, thus leaving the composition substantially DMSO-free, and to avoid any potential harmful effects that DMSO may have. The combined composition may then be cryogenically stored, for example, in cryogenic vials in an ultra-low freezer. The cryogenic storage may be controlled at a temperature below −60° C., or below −80° C.

Figure 11:
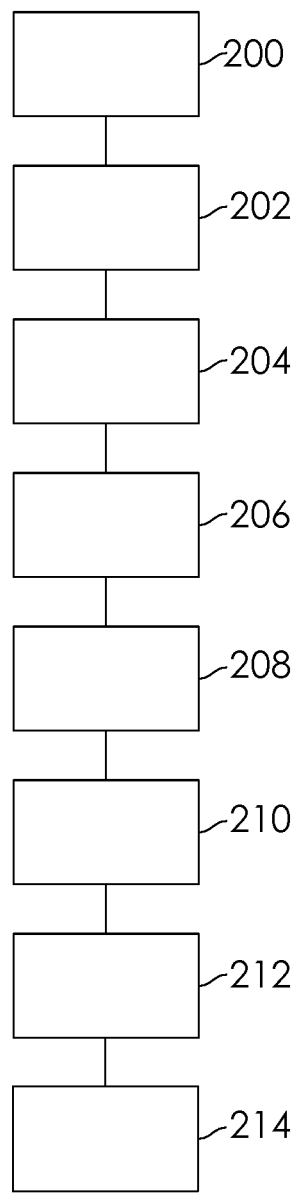
FIG. 11 illustrates a process for forming a composition for implantation within a patient according to a third embodiment.

A method of producing compositions such as the embodiments described herein is described according to a third embodiment. In step 200 of FIG. 11, a sample comprising human umbilical cord blood and having a first volume $V_{UC}$ is obtained. The human umbilical cord blood typically includes red blood cells, cells other than red blood cells, and non-cellular material. In step 202, the sample comprising human umbilical cord blood 271 is mixed with a volume $V_{PC}$ of PrepaCyte®-CB solution 273, Bio-E, LLC, Bloomington, Minn., or an equivalent aggregation agent or sedimentation agent, within a first flexible container 267, as shown in FIG. 12. A spike 277 and insertion tube 279 connected to the first flexible container 267 may be utilized to insert the sample comprising human umbilical cord blood 271, or even the volume Vpc of PrepaCyte®-CB solution 273. In some embodiments, the volume $V_{PC}$ of PrepaCyte®-CB solution 273 is received already within the first flexible container 267. Either or both of the volumes $V_{UC}$ and $V_{PC}$ may be selected such that the ratio $V_{UC}/V_{PC}$ is between about 0.60 and about 1.75. In some embodiments, the ratio $V_{UC}/V_{PC}$ is between about 0.75 and about 1.25. In some embodiments, the ratio $V_{UC}/V_{PC}$ is between about 0.60 and about 1.10. In some embodiments, the ratio $V_{UC}/V_{PC}$ is between about 1.25 and about 1.75. In step 204, the mixed volumes $V_{UC}+V_{PC}$ are allowed to remain in the first flexible container for at least 20 minutes, until a supernatant 275 is formed. In some embodiments, the mixed volumes $V_{UC}+V_{PC}$ are allowed to remain in the first flexible container 267 for at least 30 minutes. In step 206, at least a portion of the supernatant 275 is forced from the from the first flexible container 267 into a second flexible container 268 (arrow) via a conduit 269 which links the first flexible container 267 to the second flexible container 268, as shown in FIG. 14. In step 208, the second flexible container 268 is placed in a centrifuge and the centrifuge is operated to apply a centrifugal force on the supernatant within the second flexible container 268. In some embodiments, the first flexible container 267 may be removed from the second flexible container 268 and discarded, for example, by cutting the conduit 269. The portion of the cut conduit 269 extending from the second flexible container 268 may be clamped off after cutting. A sufficient centrifugal force component 278 is placed on the second flexible container 268 (FIG. 13) and its contents, with the centrifugal force component 278 directed toward a closed container end 280, to cause layering as shown in FIG. 15 to form. FIG. 13 illustrates the basic mechanics of a centrifuge 46 which spins the second flexible container 268 in a circular path 282 around a center point 284. The second flexible container 268 may, for example, be carefully placed within the centrifuge 46 in an appropriate location for spinning. In FIG. 15, a layer 286 comprises granulocytes and erythrocytes and a layer 272a contains the remaining PrepaCyte®-CB solution 273. Layer 288 substantially comprises mononuclear cells, and layer 290 substantially comprises plasma and platelets. In some embodiments, step 208 may be performed using a centrifuge which places at least about 350 times the acceleration due to gravity on the second flexible container 268 and its contents. In some embodiments, step 208 may be performed using a centrifuge which places at least about 400 times the acceleration due to gravity on the second flexible container 268 and its contents. In some embodiments, step 208 may be performed using a centrifuge which places at least about 450 times the acceleration due to gravity on the second flexible container 268 and its contents. In some embodiments, step 208 may be performed using a centrifuge which places at least about 600 times the acceleration due to gravity on the second flexible container 268 and its contents. In some embodiments, step 208 may be performed using a centrifuge which places at least about 800 times the acceleration due to gravity on the second flexible container 268 and its contents. In some embodiments, step 208 may be performed using a centrifuge which places at least about 1,400 times the acceleration due to gravity on the container 268 and its contents. In some embodiments, the centrifuge may be run between about 5 minutes and about 30 minutes to achieve the desired result.

In addition to controlling the amount of centrifugal force on the contents and/or the amount of time that the centrifuge is operated, a user may also choose to control the ramp up and ramp down of the centrifuge; in other words, the time required to reach the chosen centrifugal force from a stopped condition, and the time required to reach a stopped condition from the nominally chosen centrifugal force. In a traditional centrifuge, this corresponds to the speeding up of the rotational speed (e.g., RPM) until a desired constant operation rate is reached, and the slowing down of the rotational speed (from a desired constant operation rate) to a stopped condition. The control of one or both of these two elements can be used to further optimize the effectiveness of the centrifugation. The time to ramp up to a desired centrifugal force from substantially zero centrifugal force may be between about 30 seconds and about 15 minutes, or between about one minute and about five minutes. The time to ramp down from a desired centrifugal force to substantially zero centrifugal force may be between about 30 seconds and about 20 minutes, or between about one minute and about 10 minutes.

In step 210, mononuclear cells from the mononuclear cell layer 288 are removed from the second flexible container 268 and are combined with a reagent to create a mononuclear cell solution. In some embodiments, the reagent comprises human serum, for example, 5% human serum albumin. Prior to the removal of the mononuclear cells from the second flexible container 268, the layer 290 may be first removed, thus making it easier to remove the layer 288. Care can be taken so that the layer 288 is not disturbed when removing the layer 290, for example, by use of a sterile pipette. The layer 290 may also be carefully removed (e.g. by aspiration with a needle) through an additional access tube 281 having a port or valve 283. In some embodiments, the mononuclear cell solution substantially comprises non-expanded cell populations. In some embodiments, the mononuclear cell solution comprises non-pooled cell populations. It should be noted that the layer 290 is substantially removed prior to removing the mononuclear cells from the layer 288 to minimize any unnecessary contamination by platelets or plasma proteins. It should also be noted that the layer 272a is left substantially undisturbed when removing the layer 288, thus minimizing any unnecessary contamination by the granulocytes in layer 286.

In step 212, a volume $V_M$ of either a portion of the mononuclear cell solution or substantially all of the mononuclear cell solution is used in order to estimate the number $N_L$ of live cells in the volume $V_M$. In some embodiments, the estimating is done by performing a CD34+ count. In some embodiments, the estimating is done by performing a Total Nucleated Cell (TNC) count. In some embodiments, the estimating is done at least in part with an automated cell counter. Alternative methods may be used for performing the cell count, including: a hemtocytometer following trypan blue staining, an ATP test, Calcein AM, a clonogenic assay, an ethidium homodimer assay, Evans blue, fluorescein diacetate hydrolysis/propidium iodide staining (FDA/PI staining), flow cytometry, formazan-based-assays (MTT/XTT), green fluorescent protein, lactate dehydrogenase (LDH), methyl violet, propidium iodide DNA stain (to differentiate necrotic, apoptotic, and normal cells), resazurin, trypan blue which only crosses cell membranes of dead cells, or TUNEL assay. At the end of step 212 substantially all of the reagent may be removed from the volume $V_M$.

In step 214, albumin is added to the combined composition. In some embodiments, between about 10 mg and about 150 mg of albumin may be added per one milliliter of the combined composition. In some embodiments, between about 10 mg and about 120 mg of albumin may be added per one milliliter of the combined composition. In some embodiments, between about 50 mg and about 150 mg of albumin may be added per one milliliter of the combined composition. In some embodiments, between about 50 mg and about 120 mg of albumin may be added per one milliliter of the combined composition. In some embodiments, between about 80 mg and about 150 mg of albumin may be added per one milliliter of the combined composition. In some embodiments, between about 80 mg and about 120 mg of albumin may be added per one milliliter of the combined composition. In some embodiments, between about 105 mg and about 150 mg of albumin may be added per one milliliter of the combined composition. In some embodiments, between about 105 mg and about 120 mg of albumin may be added per one milliliter of the combined composition. In some embodiments, between about 15 mg and about 30 mg of albumin may be added per one milliliter of the combined composition. In some embodiments, between about 18 mg and about 25 mg of albumin may be added per one milliliter of the combined composition. In some embodiments, about 20 mg of albumin may be added per one milliliter of the combined composition.

In some embodiments, Low Molecular Weight Dextran in Dextrose solution is added to the volume $V_M$ of the at least a portion of the mononuclear cell solution during or prior to the addition of albumin. In some embodiments, the amount of Low Molecular Weight Dextran in Dextrose solution is based at least partially upon the estimated number $N_L$ of live cells, a calculated, estimated or determined. In some embodiments, the calculation, estimation or determination of the volume $V_{DD}$ pf the Low Molecular Weight Dextran in Dextrose solution added may be at least partially based on the assumption that approximately 75% of cells in the at least a portion mononuclear cell solution will be viable following freezing and thawing. In some embodiments, the calculation, estimation or determination of the volume $V_{DD}$ may be at least partially based on an intended live cell concentration of between about 100,000 live cells and about 75 million live cells per milliliter. In some embodiments, the calculation, estimation or determination of the volume $V_{DD}$ may be at least partially based on an intended live cell concentration of between about 750,000 live cells and about 30 million live cells per milliliter. In some embodiments, the cells may be stored cryogenically. In some embodiments, the calculation, estimation or determination of the volume $V_{DD}$ may be at least partially based on an intended live cell concentration of between about 10 million live cells and about 30 million live cells per milliliter. In some embodiments, the calculation, estimation or determination of the volume $V_{DD}$ may be at least partially based on an intended live cell concentration of between about 10 million live cells and about 20 million live cells per milliliter. In some embodiments, the cryogenic storage is below about −60° C. In some embodiments, the cryogenic storage is below about −80° C.

In some embodiments, the pH of the combined composition may be adjusted if needed, in order to produce a pH within a desired range. In some embodiments, the pH is adjusted by adding a sodium bicarbonate, such as sodium bicarbonate powder. In some embodiments, the pH is adjusted by adding a calcium bicarbonate, such as calcium bicarbonate solution. In some embodiments, the pH is adjusted to or maintained at between 4.1 and 8.5. In some embodiments, the pH is adjusted to or maintained at between 4.1 and 7.2. In some embodiments, the pH is adjusted to or maintained at between 4.1 and 6.2. In some embodiments, the pH is adjusted to or maintained at between 5.0 and 7.4. In some embodiments, the pH is adjusted to or maintained at between 5.0 and 7.2. In some embodiments, the pH is adjusted to or maintained at between 5.0 and 6.2.

In some embodiments, the mononuclear cell solution comprises stem cells. In some embodiments, the stem cells comprise hemapoietic stem cells (HSC). In some embodiments, the stem cells comprise mesenchymal stem cells (MSC).

In some embodiments, one or more bioactive agents may be added to the composition. The one or more bioactive agents may include cytokines or growth factors, and may be derived from human umbilical cord blood. In some embodiments, the one or more bioactive agents may be obtained or derived from the same sample comprising human umbilical cord blood that is described in step 200. In some embodiments, the one or more bioactive agents may be obtained or derived from human umbilical cord blood that is not the sample comprising human umbilical cord blood that is described in step 200. In some embodiments, the one or more bioactive agents may be obtained or derived from human umbilical cord blood that is from a different donor than the sample comprising human umbilical cord blood that is described in step 200. In some embodiments, the one or more bioactive agents are obtained or derived from commercially available human albumin or commercially available human albumin serum.

In some embodiments, the one or more bioactive agents may include but are not limited to cytokines or growth factors. The bioactive agents may include any of the following: chemokines, including macrophage inflammatory protein alpha (MIP-1α), macrophage inflammatory protein beta (MIP-1β), interferon gamma-induced protein 10 (IP-10), interleukins, including interleukin 1 Beta (IL-1β), interleukin 2 (IL-2), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 12 (IL-12), interleukin 13 (IL-13), interleukin 15 (IL-15), interleukin 17 (IL-17), interleukin 18 (IL-18), interleukin 21 (IL-21), interleukin 22 (IL-22), interleukin 23 (IL- 23), interleukin 27 (IL-27), interleukin 31 (IL-31), interferons, including interferon alpha (INFα), a lymphokine, granulocyte macrophage colony stimulating factor (GM-CSF), stem cell factor (KL), tumor necrosis factor alpha (TNF-α), vascular endothelial growth factor (VEGF), nerve growth factor, platelet-derived growth factor (PDGF), fibroblast growth factor 2 (FGF-2), epidermal growth factor (EGF), keratinocyte growth factor, transforming growth factor (TGF), insulin-like growth factor, des(1-3)-IGF-I (brain IGF-I), neurotrophin-3 (NT-3), brain-derived neurotrophic factor (BDNF), eotaxin, CXC ligand 1 (GROα), interleukin 1 receptor antagonist (IL-1RA), interleukin 1 alpha (IL-1α), leukemia inhibitory factor (LIF), placental growth factor (PLGF), chemokine ligand 5 (RANTES), stem cell factor (SCF), stromal cell derived factor (SDF1α), and tumor necrosis factor (TNF β).

In some embodiments, dimethyl sulfoxide (DMSO) is not added into the composition in any of the steps, thus leaving the composition substantially DMSO-free, and to avoid any potential harmful effects that DMSO may have. The combined composition may then be cryogenically stored, for example, in cryogenic vials in an ultra-low freezer. The cryogenic storage may be controlled at a temperature below −60° C., or below −80° C.

Figure 16:
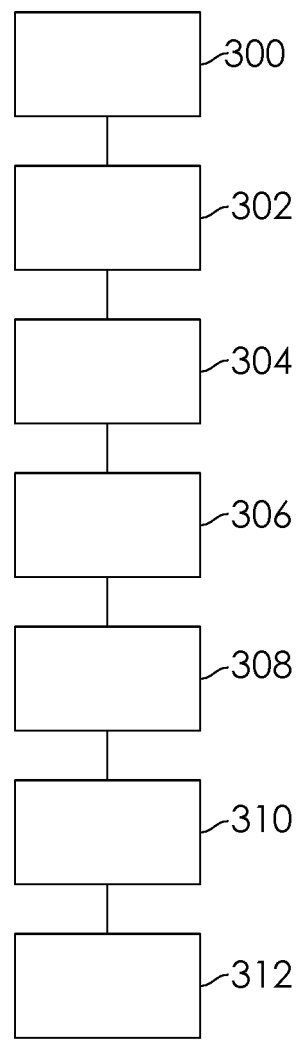
FIG. 16 illustrates a process for forming a composition for implantation within a patient according to a fourth embodiment.

A method of producing compositions such as the embodiments described herein is described according to a fourth embodiment. In step 300 of FIG. 16, a sample comprising human umbilical cord blood and having a first volume $V_{UC}$ is obtained. The human umbilical cord blood typically includes red blood cells, cells other than red blood cells, and non-cellular material. In step 302, the sample comprising human umbilical cord blood is combined with a volume $V_{PC}$ of PrepaCyte®-CB solution, Bio-E, LLC, Bloomington, Minn., or an equivalent aggregation agent or sedimentation agent. Either of both of the volumes $V_{UC}$ and $V_{PC}$ may be selected such that the ratio $V_{UC}/V_{PC}$ is between about 0.60 and about 1.75. In some embodiments, the ratio $V_{UC}/V_{PC}$ is between about 0.75 and about 1.25. In some embodiments, the ratio $V_{UC}/V_{PC}$ is between about 0.60 and about 1.10. In some embodiments, the ratio $V_{UC}/V_{PC}$ is between about 1.25 and about 1.75. The combined volumes $V_{UC}$ and $V_{PC}$ are allowed to stand undisturbed for at least about 20 minutes, or at least about 30 minutes, until a supernatant is formed, or until at least two distinct layers are formed. In step 304, a container 368 configured to be subjected to a centrifugal force (e.g., a centrifuge tube) is partially filled with a reagent 370 (FIG. 17) which is configured for isolating mononuclear cells, the reagent 370 having a volume $V_R$. In some embodiments, the reagent 370 comprises Ficoll-Paque® Centrifugation Media, GE Healthcare Bio-Sciences AB, Uppsala, Sweden, or equivalent media. In some embodiments, the reagent 370 comprises Ficoll-Paque® PLUS Centrifugation Media. In some embodiments, the reagent 370 comprises Ficoll-Paque® PREMIUM Centrifugation Media. In some embodiments, the reagent 370 has a density of between about 1.0 grams/ml and about 1.3 grams/ml. In some embodiments, the reagent 370 has a density of between about 1.07 grams/ml and about 1.09 grams/ml. In some embodiments, the reagent 370 has a density of between about 1.073 grams/ml and about 1.084 grams/ml. The volume $V_R$ of the reagent 370 represents a first layer 372 (e.g., bottom layer) in the container 368. Further, as part of step 304, a second layer 374 comprising a volume $V_S$ of the supernatant 376 produced in step 302 is layered over first layer 372 in the container 368, as shown in FIG. 17. The layer 372 of the reagent 370 is layered with a height, or column height $CH_R$, that is at least 67% of the height, or column height $CH_S$, of the layer 374 of the supernatant 376. In some embodiments, the column height $CH_R$ of the layer 372 of the reagent 370 is at least 75% of the column height $CH_S$ of the layer 374 of the supernatant 376. In some embodiments, the column height $CH_R$ of the layer 372 of the reagent 370 is at least 85% of the column height $CH_S$ of the layer 374 of the supernatant 376. In some embodiments, the column height $CH_R$ of the layer 372 of the reagent 370 is between about 30% and about 135% of the column height $CH_S$ of the layer 374 of the supernatant 376. In some embodiments, the column height $CH_R$ of the layer 372 of the reagent 370 is between about 50% and about 100% of the column height $CH_S$ of the layer 374 of the supernatant 376. In some embodiments, the column height $CH_R$ of the layer 372 of the reagent 370 is between about 75% and about 100% of the column height $CH_S$ of the layer 374 of the supernatant 376. The second layer 374 should be added over the first layer 372 in a slow or at least gentle or non-disruptive manner (e.g., slow speed pipetting) if a distinct interface between the two layers 372, 374 is initially desired.

In step 306, a sufficient centrifugal force component 378 is placed on the container 368 (FIG. 18) and its contents (e.g., first layer 372 and second layer 374), with the centrifugal force component 378 directed toward a closed container end 380, to cause layering as shown in FIG. 19 to form. FIG. 18 illustrates the basic mechanics of a centrifuge 46 which spins the container 368 in a circular path 382 around a center point 384. The container 368 may, for example, be carefully placed within the centrifuge 46 in an appropriate location for spinning. In FIG. 19, a layer 386 comprises granulocytes and erythrocytes, and has migrated below a layer 372a containing the reagent 370, and which remains from the first layer 372 of FIG. 17. Layer 388 substantially comprises mononuclear cells, and layer 390 substantially comprises plasma and platelets. In some embodiments, step 306 may be performed using a centrifuge which places at least about 350 times the acceleration due to gravity on the container 368 and its contents. In some embodiments, step 306 may be performed using a centrifuge which places at least about 400 times the acceleration due to gravity on the container 368 and its contents. In some embodiments, step 306 may be performed using a centrifuge which places at least about 450 times the acceleration due to gravity on the container 368 and its contents. In some embodiments, step 306 may be performed using a centrifuge which places at least about 600 times the acceleration due to gravity on the container 368 and its contents. In some embodiments, step 306 may be performed using a centrifuge which places at least about 800 times the acceleration due to gravity on the container 368 and its contents. In some embodiments, step 306 may be performed using a centrifuge which places at least about 1,400 times the acceleration due to gravity on the container 368 and its contents. In some embodiments, the centrifuge may be run between about 5 minutes and about 30 minutes to achieve the desired result.

In addition to controlling the amount of centrifugal force on the contents and/or the amount of time that the centrifuge is operated, a user may also choose to control the ramp up and ramp down of the centrifuge; in other words, the time required to reach the chosen centrifugal force from a stopped condition, and the time required to reach a stopped condition from the nominally chosen centrifugal force. In a traditional centrifuge, this corresponds to the speeding up of the rotational speed (e.g., RPM) until a desired constant operation rate is reached, and the slowing down of the rotational speed (from a desired constant operation rate) to a stopped condition. The control of one or both of these two elements can be used to further optimize the effectiveness of the centrifugation. The time to ramp up to a desired centrifugal force from substantially zero centrifugal force may be between about 30 seconds and about 15 minutes, or between about one minute and about five minutes. The time to ramp down from a desired centrifugal force to substantially zero centrifugal force may be between about 30 seconds and about 20 minutes, or between about one minute and about 10 minutes.

In step 308, mononuclear cells from the mononuclear cell layer 388 are removed from the container 368 and are combined with lactated Ringer's solution, to create a mononuclear cell solution. Prior to the removal of the mononuclear cells from the container 368, the layer 390 may be first removed (FIG. 20), thus making it easier to remove the layer 388. Care can be taken so that the layer 388 is not disturbed when removing the layer 390, for example, by use of a sterile pipette. In step 308, the mononuclear cells from the mononuclear cell layer 388 are actively (though gently) mixed with the lactated Ringer's solution. The mononuclear cells may also be washed one, two, or more times with lactated Ringer's solution. In some embodiments, the mononuclear cell solution substantially comprises non-expanded cell populations. In some embodiments, the mononuclear cell solution comprises non-pooled cell populations. It should be noted that the layer 390 is substantially removed prior to removing the mononuclear cells from the layer 388 to minimize any unnecessary contamination by platelets or plasma proteins. It should also be noted that the layer 372a is left substantially undisturbed when removing the layer 388, thus minimizing any unnecessary contamination by the granulocytes in layer 386.

In step 310, a volume $V_M$ of either a portion of the mononuclear cell solution or substantially all of the mononuclear cell solution is used in order to estimate the number $N_L$ of live cells in the volume $V_M$. In some embodiments, the estimating is done by performing a CD34+ count. In some embodiments, the estimating is done by performing a Total Nucleated Cell (TNC) count. In some embodiments, the estimating is done at least in part with an automated cell counter. Alternative methods may be used for performing the cell count, including: a hemtocytometer following trypan blue staining, an ATP test, Calcein AM, a clonogenic assay, an ethidium homodimer assay, Evans blue, fluorescein diacetate hydrolysis/propidium iodide staining (FDA/PI staining), flow cytometry, formazan-based-assays (MTT/XTT), green fluorescent protein, lactate dehydrogenase (LDH), methyl violet, propidium iodide DNA stain (to differentiate necrotic, apoptotic, and normal cells), resazurin, trypan blue which only crosses cell membranes of dead cells, or TUNEL assay. At the end of step 310 substantially all of the lactated Ringer's solution may be removed from the volume $V_M$.

In step 312, albumin is added to the combined composition. In some embodiments, between about 10 mg and about 150 mg of albumin may be added per one milliliter of the combined composition. In some embodiments, between about 10 mg and about 120 mg of albumin may be added per one milliliter of the combined composition. In some embodiments, between about 50 mg and about 150 mg of albumin may be added per one milliliter of the combined composition. In some embodiments, between about 50 mg and about 120 mg of albumin may be added per one milliliter of the combined composition. In some embodiments, between about 80 mg and about 150 mg of albumin may be added per one milliliter of the combined composition. In some embodiments, between about 80 mg and about 120 mg of albumin may be added per one milliliter of the combined composition. In some embodiments, between about 105 mg and about 150 mg of albumin may be added per one milliliter of the combined composition. In some embodiments, between about 105 mg and about 120 mg of albumin may be added per one milliliter of the combined composition. In some embodiments, between about 15 mg and about 30 mg of albumin may be added per one milliliter of the combined composition. In some embodiments, between about 18 mg and about 25 mg of albumin may be added per one milliliter of the combined composition. In some embodiments, about 20 mg of albumin may be added per one milliliter of the combined composition.

In some embodiments, Low Molecular Weight Dextran in Dextrose solution is added to the volume $V_M$ of the at least a portion of the mononuclear cell solution during or prior to the addition of albumin. In some embodiments, the amount of Low Molecular Weight Dextran in Dextrose solution is based at least partially upon the estimated number $N_L$ of live cells, a calculated, estimated or determined. In some embodiments, the calculation, estimation or determination of the volume $V_{DD}$ pf the Low Molecular Weight Dextran in Dextrose solution added may be at least partially based on the assumption that approximately 75% of cells in the at least a portion mononuclear cell solution will be viable following freezing and thawing. In some embodiments, the calculation, estimation or determination of the volume $V_{DD}$ may be at least partially based on an intended live cell concentration of between about 100,000 live cells and about 75 million live cells per milliliter. In some embodiments, the calculation, estimation or determination of the volume $V_{DD}$ may be at least partially based on an intended live cell concentration of between about 750,000 live cells and about 30 million live cells per milliliter. In some embodiments, the cells may be stored cryogenically. In some embodiments, the calculation, estimation or determination of the volume $V_{DD}$ may be at least partially based on an intended live cell concentration of between about 10 million live cells and about 30 million live cells per milliliter. In some embodiments, the calculation, estimation or determination of the volume $V_{DD}$ may be at least partially based on an intended live cell concentration of between about 10 million live cells and about 20 million live cells per milliliter. In some embodiments, the cryogenic storage is below about −60° C. In some embodiments, the cryogenic storage is below about −80° C.

In some embodiments, the pH of the combined composition may be adjusted if needed, in order to produce a pH within a desired range. In some embodiments, the pH is adjusted by adding a sodium bicarbonate, such as sodium bicarbonate powder. In some embodiments, the pH is adjusted by adding a calcium bicarbonate, such as calcium bicarbonate solution. In some embodiments, the pH is adjusted to or maintained at between 4.1 and 8.5. In some embodiments, the pH is adjusted to or maintained at between 4.1 and 7.2. In some embodiments, the pH is adjusted to or maintained at between 4.1 and 6.2. In some embodiments, the pH is adjusted to or maintained at between 5.0 and 7.4. In some embodiments, the pH is adjusted to or maintained at between 5.0 and 7.2. In some embodiments, the pH is adjusted to or maintained at between 5.0 and 6.2.

In some embodiments, the mononuclear cell solution comprises stem cells. In some embodiments, the stem cells comprise hemapoietic stem cells (HSC). In some embodiments, the stem cells comprise mesenchymal stem cells (MSC).

In some embodiments, one or more bioactive agents may be added to the composition. The one or more bioactive agents may include cytokines or growth factors, and may be derived from human umbilical cord blood. In some embodiments, the one or more bioactive agents may be obtained or derived from the same sample comprising human umbilical cord blood that is described in step 300. In some embodiments, the one or more bioactive agents may be obtained or derived from human umbilical cord blood that is not the sample comprising human umbilical cord blood that is described in step 300. In some embodiments, the one or more bioactive agents may be obtained or derived from human umbilical cord blood that is from a different donor than the sample comprising human umbilical cord blood that is described in step 300. In some embodiments, the one or more bioactive agents are obtained or derived from commercially available human albumin or commercially available human albumin serum.

In some embodiments, the one or more bioactive agents may include but are not limited to cytokines or growth factors. The bioactive agents may include any of the following: chemokines, including macrophage inflammatory protein alpha (MIP-1α), macrophage inflammatory protein beta (MIP-1β), interferon gamma-induced protein 10 (IP-10), interleukins, including interleukin 1 Beta (IL-1β), interleukin 2 (IL-2), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 12 (IL-12), interleukin 13 (IL-13), interleukin 15 (IL-15), interleukin 17 (IL-17), interleukin 18 (IL-18), interleukin 21 (IL-21), interleukin 22 (IL-22), interleukin 23 (IL-23), interleukin 27 (IL-27), interleukin 31 (IL-31), interferons, including interferon alpha (INFα), a lymphokine, granulocyte macrophage colony stimulating factor (GM-CSF), stem cell factor (KL), tumor necrosis factor alpha (TNF-α), vascular endothelial growth factor (VEGF), nerve growth factor, platelet-derived growth factor (PDGF), fibroblast growth factor 2 (FGF-2), epidermal growth factor (EGF), keratinocyte growth factor, transforming growth factor (TGF), insulin-like growth factor, des(1-3)-IGF-I (brain IGF-I), neurotrophin-3 (NT-3), brain-derived neurotrophic factor (BDNF), eotaxin, CXC ligand 1 (GROα), interleukin 1 receptor antagonist (IL-1RA), interleukin 1 alpha (IL-1α), leukemia inhibitory factor (LIF), placental growth factor (PLGF), chemokine ligand 5 (RANTES), stem cell factor (SCF), stromal cell derived factor (SDF1α), and tumor necrosis factor (TNF β).

In some embodiments, dimethyl sulfoxide (DMSO) is not added into the composition in any of the steps, thus leaving the composition substantially DMSO-free, and to avoid any potential harmful effects that DMSO may have. The combined composition may then be cryogenically stored, for example, in cryogenic vials in an ultra-low freezer. The cryogenic storage may be controlled at a temperature below −60° C., or below −80° C.

Figure 21:
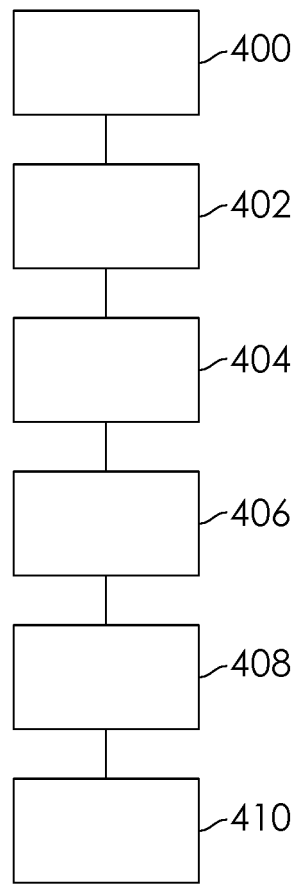
FIG. 21 illustrates a process for forming a composition for implantation within a patient according to a fifth embodiment.

A method of producing compositions such as the embodiments described herein is described according to a fifth embodiment. In step 400 of FIG. 21, a sample comprising human umbilical cord blood and having a first volume $V_{UC}$ is obtained. The human umbilical cord blood typically includes red blood cells, cells other than red blood cells, and non-cellular material. In step 402, the sample comprising human umbilical cord blood is combined with a volume $V_{PC}$ of PrepaCyte®-CB solution, Bio-E, LLC, Bloomington, Minn., or an equivalent aggregation agent or sedimentation agent. Either or both of the volumes $V_{UC}$ and $V_{PC}$ may be selected such that the ratio $V_{UC}/V_{PC}$ is between about 0.60 and about 1.75. In some embodiments, the ratio $V_{UC}/V_{PC}$ is between about 0.75 and about 1.25. In some embodiments, the ratio $V_{UC}/V_{PC}$ is between about 0.60 and about 1.10. The combined volumes $V_{UC}$ and $V_{PC}$ are allowed to stand undisturbed for at least about 20 minutes, or at least about 30 minutes, until a supernatant is formed, or until at least two distinct layers are formed. In step 404, a container 468 configured to be subjected to a centrifugal force (e.g., a centrifuge tube) is partially filled with a reagent 470 (FIG. 22) which is configured for isolating mononuclear cells, the reagent 470 having a volume $V_R$. In some embodiments, the reagent 470 comprises Ficoll-Paque® Centrifugation Media, GE Healthcare Bio-Sciences AB, Uppsala, Sweden, or equivalent media. In some embodiments, the reagent 470 comprises Ficoll-Paque® PLUS Centrifugation Media. In some embodiments, the reagent 470 comprises Ficoll-Paque® PREMIUM Centrifugation Media. In some embodiments, the reagent 470 has a density of between about 1.0 grams/ml and about 1.3 grams/ml. In some embodiments, the reagent 470 has a density of between about 1.07 grams/ml and about 1.09 grams/ml. In some embodiments, the reagent 470 has a density of between about 1.073 grams/ml and about 1.084 grams/ml. The volume $V_R$ of the reagent 470 represents a first layer 472 (e.g., bottom layer) in the container 468. Further, as part of step 404, a second layer 474 comprising a volume $V_S$ of the supernatant 476 produced in step 402 is layered over first layer 472 in the container 468, as shown in FIG. 22. The layer 472 of the reagent 470 is layered with a height, or column height $CH_R$, that is at least 67% of the height, or column height $CH_S$, of the layer 474 of the supernatant 476. In some embodiments, the column height $CH_R$ of the layer 472 of the reagent 470 is at least 75% of the column height $CH_S$ of the layer 474 of the supernatant 476. In some embodiments, the column height $CH_R$ of the layer 472 of the reagent 470 is at least 85% of the column height $CH_S$ of the layer 474 of the supernatant 476. In some embodiments, the column height $CH_R$ of the layer 472 of the reagent 470 is between about 30% and about 135% of the column height $CH_S$ of the layer 474 of the supernatant 476. In some embodiments, the column height $CH_R$ of the layer 472 of the reagent 470 is between about 50% and about 100% of the column height $CH_S$ of the layer 474 of the supernatant 476. In some embodiments, the column height $CH_R$ of the layer 472 of the reagent 470 is between about 75% and about 100% of the column height $CH_S$ of the layer 474 of the supernatant 476. The second layer 474 should be added over the first layer 472 in a slow or at least gentle or non-disruptive manner (e.g., slow speed pipetting) if a distinct interface between the two layers 472, 474 is initially desired.

In step 406, a sufficient centrifugal force component 478 is placed on the container 468 (FIG. 23) and its contents (e.g., first layer 472 and second layer 474), with the centrifugal force component 478 directed toward a closed container end 480, to cause layering as shown in FIG. 24 to form. FIG. 23 illustrates the basic mechanics of a centrifuge 46 which spins the container 468 in a circular path 482 around a center point 484. The container 468 may, for example, be carefully placed within the centrifuge 46 in an appropriate location for spinning. In FIG. 24, a layer 486 comprises granulocytes and erythrocytes, and has migrated below a layer 472a containing the reagent 470, and which remains from the first layer 472 of FIG. 22. Layer 488 substantially comprises mononuclear cells, and layer 490 substantially comprises plasma and platelets. In some embodiments, step 406 may be performed using a centrifuge which places at least about 350 times the acceleration due to gravity on the container 468 and its contents. In some embodiments, step 406 may be performed using a centrifuge which places at least about 400 times the acceleration due to gravity on the container 468 and its contents. In some embodiments, step 406 may be performed using a centrifuge which places at least about 450 times the acceleration due to gravity on the container 468 and its contents. In some embodiments, step 406 may be performed using a centrifuge which places at least about 600 times the acceleration due to gravity on the container 468 and its contents. In some embodiments, step 406 may be performed using a centrifuge which places at least about 800 times the acceleration due to gravity on the container 468 and its contents. In some embodiments, step 406 may be performed using a centrifuge which places at least about 1,400 times the acceleration due to gravity on the container 468 and its contents. In some embodiments, the centrifuge may be run between about 5 minutes and about 30 minutes to achieve the desired result.

In addition to controlling the amount of centrifugal force on the contents and/or the amount of time that the centrifuge is operated, a user may also choose to control the ramp up and ramp down of the centrifuge; in other words, the time required to reach the chosen centrifugal force from a stopped condition, and the time required to reach a stopped condition from the nominally chosen centrifugal force. In a traditional centrifuge, this corresponds to the speeding up of the rotational speed (e.g., RPM) until a desired constant operation rate is reached, and the slowing down of the rotational speed (from a desired constant operation rate) to a stopped condition. The control of one or both of these two elements can be used to further optimize the effectiveness of the centrifugation. The time to ramp up to a desired centrifugal force from substantially zero centrifugal force may be between about 30 seconds and about 15 minutes, or between about one minute and about five minutes. The time to ramp down from a desired centrifugal force to substantially zero centrifugal force may be between about 30 seconds and about 20 minutes, or between about one minute and about 10 minutes.

In step 408, mononuclear cells from the mononuclear cell layer 488 are removed from the container 468 and are combined with lactated Ringer's solution, to create a mononuclear cell solution. Prior to the removal of the mononuclear cells from the container 468, the layer 490 may be first removed (FIG. 25), thus making it easier to remove the layer 488. Care can be taken so that the layer 488 is not disturbed when removing the layer 490, for example, by use of a sterile pipette. In step 408, the mononuclear cells from the mononuclear cell layer 488 are actively (though gently) mixed with the lactated Ringer's solution. The mononuclear cells may also be washed one, two, or more times with lactated Ringer's solution. In some embodiments, the mononuclear cell solution substantially comprises non-expanded cell populations. In some embodiments, the mononuclear cell solution comprises non-pooled cell populations. It should be noted that the layer 490 is substantially removed prior to removing the mononuclear cells from the layer 488 to minimize any unnecessary contamination by platelets or plasma proteins. It should also be noted that the layer 472*a* is left substantially undisturbed when removing the layer 488, thus minimizing any unnecessary contamination by the granulocytes in layer 486.

In step 410, a volume $V_M$ of either a portion of the mononuclear cell solution or substantially all of the mononuclear cell solution is used in order to estimate the number $N_L$ of live cells in the volume $V_M$. In some embodiments, the estimating is done by performing a CD34+ count. In some embodiments, the estimating is done by performing a Total Nucleated Cell (TNC) count. In some embodiments, the estimating is done at least in part with an automated cell counter. Alternative methods may be used for performing the cell count, including: a hemtocytometer following trypan blue staining, an ATP test, Calcein AM, a clonogenic assay, an ethidium homodimer assay, Evans blue, fluorescein diacetate hydrolysis/propidium iodide staining (FDA/PI staining), flow cytometry, formazan-based-assays (MTT/XTT), green fluorescent protein, lactate dehydrogenase (LDH), methyl violet, propidium iodide DNA stain (to differentiate necrotic, apoptotic, and normal cells), resazurin, trypan blue which only crosses cell membranes of dead cells, or TUNEL assay. At the end of step 410 substantially all of the lactated Ringer's solution may be removed from the volume $V_M$.

In some embodiments, Low Molecular Weight Dextran in Dextrose solution is added to the volume $V_M$ of the at least a portion of the mononuclear cell solution. In some embodiments, the amount of Low Molecular Weight Dextran in Dextrose solution is based at least partially upon the estimated number $N_L$ of live cells, a calculated, estimated or determined. In some embodiments, the calculation, estimation or determination of the volume $V_{DD}$ pf the Low Molecular Weight Dextran in Dextrose solution added may be at least partially based on the assumption that approximately 75% of cells in the at least a portion mononuclear cell solution will be viable following freezing and thawing. In some embodiments, the calculation, estimation or determination of the volume $V_{DD}$ may be at least partially based on an intended live cell concentration of between about 100,000 live cells and about 75 million live cells per milliliter. In some embodiments, the calculation, estimation or determination of the volume $V_{DD}$ may be at least partially based on an intended live cell concentration of between about 750,000 live cells and about 30 million live cells per milliliter. In some embodiments, the cells may be stored cryogenically. In some embodiments, the calculation, estimation or determination of the volume $V_{DD}$ may be at least partially based on an intended live cell concentration of between about 10 million live cells and about 30 million live cells per milliliter. In some embodiments, the calculation, estimation or determination of the volume $V_{DD}$ may be at least partially based on an intended live cell concentration of between about 10 million live cells and about 20 million live cells per milliliter. In some embodiments, the cryogenic storage is below about −60° C. In some embodiments, the cryogenic storage is below about −80° C.

In some embodiments, the pH of the combined composition may be adjusted if needed, in order to produce a pH within a desired range. In some embodiments, the pH is adjusted by adding a sodium bicarbonate, such as sodium bicarbonate powder. In some embodiments, the pH is adjusted by adding a calcium bicarbonate, such as calcium bicarbonate solution. In some embodiments, the pH is adjusted to or maintained at between 4.1 and 8.5. In some embodiments, the pH is adjusted to or maintained at between 4.1 and 7.2. In some embodiments, the pH is adjusted to or maintained at between 4.1 and 6.2. In some embodiments, the pH is adjusted to or maintained at between 5.0 and 7.4. In some embodiments, the pH is adjusted to or maintained at between 5.0 and 7.2. In some embodiments, the pH is adjusted to or maintained at between 5.0 and 6.2.

In some embodiments, the mononuclear cell solution comprises stem cells. In some embodiments, the stem cells comprise hemapoietic stem cells (HSC). In some embodiments, the stem cells comprise mesenchymal stem cells (MSC).

In some embodiments, one or more bioactive agents may be added to the composition. The one or more bioactive agents may include cytokines or growth factors, and may be derived from human umbilical cord blood. In some embodiments, the one or more bioactive agents may be obtained or derived from the same sample comprising human umbilical cord blood that is described in step 400. In some embodiments, the one or more bioactive agents may be obtained or derived from human umbilical cord blood that is not the sample comprising human umbilical cord blood that is described in step 400. In some embodiments, the one or more bioactive agents may be obtained or derived from human umbilical cord blood that is from a different donor than the sample comprising human umbilical cord blood that is described in step 400. In some embodiments, the one or more bioactive agents are obtained or derived from commercially available human albumin or commercially available human albumin serum.

In some embodiments, the one or more bioactive agents may include but are not limited to cytokines or growth factors. The bioactive agents may include any of the following: chemokines, including macrophage inflammatory protein alpha (MIP-1α), macrophage inflammatory protein beta (MIP-1β), interferon gamma-induced protein 10 (IP-10), interleukins, including interleukin 1 Beta (IL-1β), interleukin 2 (IL-2), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 12 (IL-12), interleukin 13 (IL-13), interleukin 15 (IL-15), interleukin 17 (IL-17), interleukin 18 (IL-18), interleukin 21 (IL-21), interleukin 22 (IL-22), interleukin 23 (IL-23), interleukin 27 (IL-27), interleukin 31 (IL-31), interferons, including interferon alpha (INFα), a lymphokine, granulocyte macrophage colony stimulating factor (GM-CSF), stem cell factor (KL), tumor necrosis factor alpha (TNF-α), vascular endothelial growth factor (VEGF), nerve growth factor, platelet-derived growth factor (PDGF), fibroblast growth factor 2 (FGF-2), epidermal growth factor (EGF), keratinocyte growth factor, transforming growth factor (TGF), insulin-like growth factor, des(1-3)-IGF-I (brain IGF-I), neurotrophin-3 (NT-3), brain-derived neurotrophic factor (BDNF), eotaxin, CXC ligand 1 (GROα), interleukin 1 receptor antagonist (IL-1RA), interleukin 1 alpha (IL-1α), leukemia inhibitory factor (LIF), placental growth factor (PLGF), chemokine ligand 5 (RANTES), stem cell factor (SCF), stromal cell derived factor (SDF1α), and tumor necrosis factor (TNF β).

In some embodiments, dimethyl sulfoxide (DMSO) is not added into the composition in any of the steps, thus leaving the composition substantially DMSO-free, and to avoid any potential harmful effects that DMSO may have. The combined composition may then be cryogenically stored, for example, in cryogenic vials in an ultra-low freezer. The cryogenic storage may be controlled at a temperature below −60° C., or below −80° C.

Figure 26A:
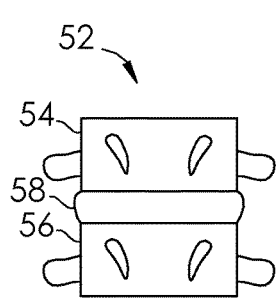
FIGS. 26A-26C illustrate two vertebrae during a spinal fusion procedure in a patient, according to an embodiment.
Figure 26B:
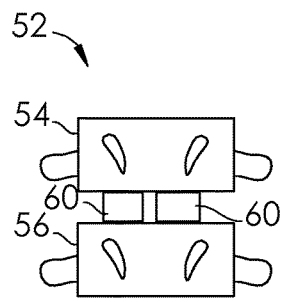
Figure 26C:
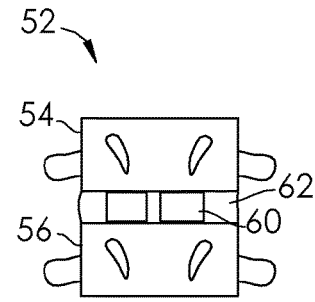

FIGS. 26A-28B illustrate compositions comprising embodiments described herein in use in medical treatment methods. FIGS. 26A-26C illustrate a procedure for spinal fusion using a composition of an embodiment described herein. A spine 52 of a patient includes two adjacent vertebrae 54, 56 which are to be fused. It may be desired to fuse two or more vertebrae to treat a number of different ailments, including, but not limited to: scoliosis, spondylolisthesis, hyperkyphosis, hyperlordosis (or hypolordosis/flat-back syndrome, hypokyphosis), degenerative disk disease (DDD), spinal stenosis, trauma, including vertebral fracture, tumor, revision surgery, infection, pseudoarthrosis, herniated disk, spondylolysis, mechanical instability, facet syndrome, chronic back pain, and radiating leg pain. In FIG. 26A, a patient's vertebrae 54, 56 are at least partially exposed and an intervertebral disk 58 is removed. In some cases, the disk 58 may already have been removed or may be missing or damaged, and thus not require removal. In some cases, at least a portion of the disk may be purposely left in place. Though in some cases it is optional, in FIG. 26B, a load-bearing device 60 is placed between the first vertebrae 54 and the second vertebrae 56. The load-bearing device 60 may include a fusion cage or interbody device. In FIG. 26C, a biological composition 62, such as any embodiment of those described herein, is placed between the vertebrae 54, 56 and, when applicable, around or adjacent to the load-bearing device 60, including within any cavities in the interbody device, should there be any. The biological composition 62, may also be placed near or at posterior-lateral gutters. Procedures may include posterior lumbar interbody fusion (PLIF), transforaminal lumbar interbody fusion (TLIF), anterior lumbar interbody fusion (ALIF), extreme lateral interbody fusion (XLIF), direct lateral interbody fusion (DLIF), or axial lumbar interbody fusion (AliaLIF). An appropriate amount of the biological composition 62 is placed so that it is effective in aiding the fusion of the two vertebrae 54, 56. In some cases the patient may be skeletally mature. In other cases, the patient may be skeletally immature.

In some cases, an effective amount of the biological composition 62 to promote, aid, or accelerate fusion of the first vertebra 54 to the second vertebra 56 may comprise between about 1% and 50% of a volume to be filled, or about 3% to 25%, or about 5% to 20%, or about 10%. The remainder of the volume to be filled may be filled with bone graft, or other materials, or left at least partially unfilled. For example, in a disc space of about 10 ml, about 0.5 ml to 2.0 ml of the biological composition 62 may be inserted, or in a disc space of about 5 ml, about 0.25 ml to about 1.0 ml of the biological composition 62 may be inserted. The biological composition 62 may be applied substantially to a particular location within the volume to be filled, or alternatively may be applied in diffuse locations within the volume to be filled. In some embodiments, other materials may be added to the biological composition 62, including synthetic bone substitutes such as beta tricalcium phosphate, or actual pieces of bone, including ground bone.

Figure 27A:
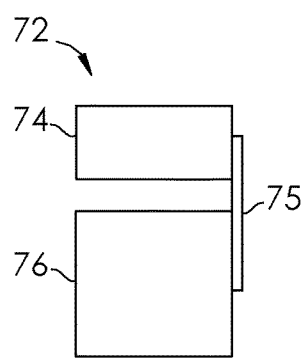
FIGS. 27A-27B illustrate two bone portions during a fusion procedure in a patient, according to an embodiment.
Figure 27B:
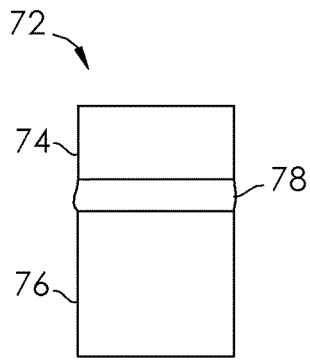

FIGS. 27A-27B illustrate a procedure for fusion using a composition of an embodiment described herein. A segment 72 of the skeletal system of a patient includes a first bone portion 74 and a second bone portion 76 which are to be fused. It may be desired to fuse two or more bone portions to treat a number of different ailments, including, but not limited to: trauma, including fracture, tumor, arthritis, ankylosis, deformity, congenital defects, bone length discrepancy, revision surgery, infection, osteonecrosis, osteoporosis, pseudoarthrosis, non-union, delayed-union, and pain. The bone portions 74, 76 may both be within a particular portion of the spine (cervical, thoracic, lumbar, sacral) or may be within two different portions (thoracic to lumbar, lumbar to sacral, etc.). In FIG. 27A, the first bone portion 74 and the second bone portion 76 are at least partially exposed. Surfaces in one or each of the first and second bone portions 74, 76 may then be prepared, for example by cutting (osteotomy) or roughening. In some cases, a load-bearing device 75, such as a plate, rod, nail, screw, hook, or pin may be used to hold the first bone portion 74 and the second bone portion 76 in relation to one another. In FIG. 27B, a biological composition 78, such as any embodiment of those described herein, is placed between the first and second bone portions 74, 76 and, when applicable, around or adjacent to the load-bearing device 75. An appropriate amount of the biological composition 78 is placed so that it is effective in aiding the fusion of first and second bone portions 74, 76. Any of the bones of the skeletal system may be fused while utilizing the biological composition 78. In some cases, the patient may be skeletally mature. In other cases, the patient may be skeletally immature.

In some cases, an effective amount of the biological composition 78 to promote, aid, or accelerate fusion of the first bone portion 74 to the second bone portion 76 may comprise between about 1% and 50% of a volume to be filled, or about 3% to 25%, or about 5% to 20%, or about 10%. The remainder of the volume to be filled may be filled with bone graft, or other materials, or left at least partially unfilled. The biological composition 78 may be applied substantially to a particular location within the volume to be filled, or alternatively may be applied in diffuse locations within the volume to be filled. In some embodiments, other materials may be added to the biological composition 78, including synthetic bone substitutes such as beta tricalcium phosphate, or actual pieces of bone, including ground bone.

Figure 28A:
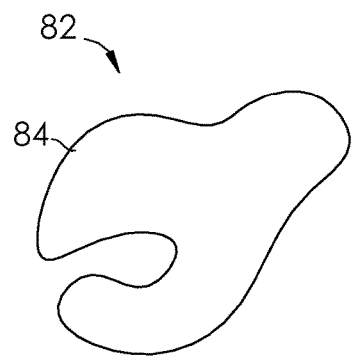
FIGS. 28A-28B illustrate soft tissue during a procedure in a patient, according to an embodiment.
Figure 28B:
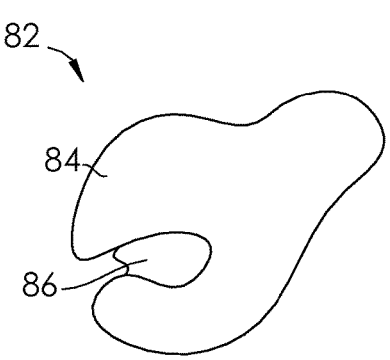

FIGS. 28A-28B illustrate a procedure for healing or growth augmentation of soft tissue 84 in a region 82 of a patient. A biological composition 86, such as any embodiment of those described herein, is placed within, near, or adjacent the soft tissue 84. In alternative procedures, partially or fully hard tissue may also or instead be treated with the biological composition 86. In some cases, the patient to be treated has at least some cancerous cells, and the biological composition 86 is placed within, near, or adjacent the cancerous cells. In some cases, the patient to be treated had at least some cancerous cells removed, and the biological composition 86 is placed within, near, or adjacent the previous location (former site) of the cancerous cells. In cancer patients or post-cancer patients, the cancer may include, but is not limited to: lymphatic cancer, including lymph vessel tumors, soft tissue sarcoma, fat tissue tumors, muscle tissue tumors, peripheral nerve tumors, fibrous tissue tumors, joint tissue tumors, and blood vessel tumors. In some cases, the biological composition may be used for vascular reconstruction (e.g., blood vessels). The patients treated may include adult or pediatric patients. In some cases, an effective amount of the biological composition 86 to promote healing or growth augmentation of the soft tissue 84 may comprise at least about 0.25 ml, or between about 0.25 ml and about 5 ml, or between about 0.25 ml and about 2 ml.

Other sources besides umbilical cord blood are possible for the compositions described herein, including, but not limited to amniotic fluid, peripheral blood, umbilical cord tissue, bone marrow, adipose tissue, and central nervous system (CNS) fluid.

In addition to previously mentioned procedures, other procedures may be performed incorporating the compositions and methods of manufacture of the embodiments described herein, including, but not limited to procedures for the treatment of diabetes mellitus and/or its related symptoms, procedures for the treatment of diabetic neuropathy, procedures for the treatment of diabetic ulcers, procedures for the treatment of epidermal, dermal, or sub-dermal diabetic ulcers, procedures for pain management for joints, including joints having chronic pain, procedures for the treatment of tendonitis, procedures for the treatment of torn cartilage, procedures for the treatment of tendon laxity, such as tendon laxity in joints, including but not limited to, shoulder joints, ankle joints, knee joints, hip joints, and elbow joints, procedures for the treatment of leukemia, procedures for the treatment of lymphoma, procedures for the treatment of myeloma, procedures for the treatment of other cancers, procedures for other epidermal, dermal, or sub-dermal disorders or illnesses, or procedures related to damage to neurons, including Parkinson's disease and brain tumors. Procedures may be performed incorporating the compositions and methods of manufacture of the embodiments described herein to reduce tumor size. The compositions may in some embodiments, be added in other manners, including epidural application, transthecal application, intravenous (IV) application, or direct site application.

While embodiments have been shown and described, various modifications may be made without departing from the scope of the inventive concepts disclosed herein.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A method for performing a medical therapy in a human subject comprising:
   providing a composition comprising:
      a low pH fluid base, wherein the low pH fluid base comprises dextrose;
      mononuclear cells obtained from human umbilical cord blood; and
      albumin, wherein the concentration of albumin is between about 10 mg/ml and about 150 mg/ml; and
   implanting within, near, or adjacent to tissue of the subject an effective amount of the composition.

2. The method of claim 1, wherein the step of implanting comprises implanting the composition between adjacent vertebrae to be fused.

3. The method of claim 2, wherein the composition is implanted in combination with a load-bearing device.

4. The method of claim 3, wherein the load-bearing device comprises a fusion cage.

5. The method of claim 3, wherein the load-bearing device comprises at least two pedicle screws and at least one rod.

6. The method of claim 2, wherein the subject is skeletally mature.

7. The method of claim 1, wherein the step of implanting comprises implanting the composition between adjacent portions of bone to be fused.

8. The method of claim 7, wherein the adjacent portions of bone comprise a first portion of bone and a second portion of bone.

9. The method of claim 8, wherein the first portion of bone is from a different bone in the skeletal system of the subject than the second portion of bone.

10. The method of claim 8, wherein the first portion of bone is from the same bone in the skeletal system of the subject as the second portion of bone.

11. The method of claim 7, wherein the composition is implanted in combination with a load-bearing device.

12. The method of claim 11, wherein the load-bearing device is selected from the list consisting of a plate, a rod, a nail, a screw, a hook, and a pin.

13. The method of claim 7, wherein the subject is skeletally mature.

14. The method of claim 1, wherein the step of implanting comprises implanting the composition within, near, or adjacent soft tissue.

15. The method of claim 1, wherein the pH of the composition is between 4.1 and 7.4.

16. The method of claim 1, wherein the composition further comprises a base configured to modify the pH of the composition.

17. The method of claim 1, wherein the low pH fluid base further comprises dimethyl sulfoxide (DMSO).

18. The method of claim 1, wherein the low pH fluid base comprises a cryopreservative.

19. The method of claim 1, wherein the low pH fluid base further comprises dextran.

20. The method of claim 1, wherein the composition further comprises stem cells.

21. The method of claim 1, wherein the composition comprises between about 100,000 and about 75 million live mononuclear cells per ml.

22. The method of claim 1, wherein the composition further comprises one or more bioactive agents.

23. The method of claim 22, wherein the one or more bioactive agents comprise one or more cytokines.

24. The method of claim 22, wherein the one or more bioactive agents comprise one or more growth factors.

25. The method of claim 22, wherein the one or more bioactive agents are selected from the group consisting of macrophage inflammatory protein alpha (MIP-1α), macrophage inflammatory protein beta (MIP-1β), interferon gamma-induced protein 10 (IP-10), interleukin 1 Beta (IL-1β), interleukin 2 (IL-2), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 12 (IL-12), interleukin 13 (IL-13), interleukin 15 (IL-15), interleukin 17 (IL-17), interleukin 18 (IL-18), interleukin 21 (IL-21), interleukin 22 (IL-22), interleukin 23 (IL-23), interleukin 27 (IL-27), interleukin 31 (IL-31), interferon alpha (INFα), a lymphokine, granulocyte macrophage colony stimulating factor (GM-CSF), stem cell factor (KL), tumor necrosis factor alpha (TNF-α), vascular endothelial growth factor (VEGF), nerve growth factor, platelet-derived growth factor (PDGF), fibroblast growth factor 2 (FGF-2), epidermal growth factor (EGF), keratinocyte growth factor, transforming growth factor (TGF), insulin-like growth factor, des(1-3)-IGF-I (brain IGF-I), neurotrophin-3 (NT-3), brain-derived neurotrophic factor (BDNF), eotaxin, CXC ligand 1 (GROa), interleukin 1 receptor antagonist (IL-1RA), interleukin 1 alpha (IL-1α), leukemia inhibitory factor (LIF), placental growth factor (PLGF), chemokine ligand 5 (RANTES), stem cell factor (SCF), stromal cell derived factor (SDF1α), and tumor necrosis factor (TNF β).

* * * * *